(12) United States Patent
Engelthaler et al.

(10) Patent No.: US 11,359,251 B2
(45) Date of Patent: Jun. 14, 2022

(54) METHODS FOR THE DETECTION OF ENTEROVIRUS D68 IN COMPLEX SAMPLES

(71) Applicant: THE TRANSLATIONAL GENOMICS RESEARCH INSTITUTE, Phoenix, AZ (US)

(72) Inventors: David Engelthaler, Flagstaff, AZ (US); Jolene Bowers, Flagstaff, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 370 days.

(21) Appl. No.: 16/041,711

(22) Filed: Jul. 20, 2018

(65) Prior Publication Data
US 2019/0024194 A1    Jan. 24, 2019

Related U.S. Application Data

(60) Provisional application No. 62/535,813, filed on Jul. 21, 2017.

(51) Int. Cl.
*C12Q 1/68*    (2018.01)
*C12Q 1/70*    (2006.01)

(52) U.S. Cl.
CPC ....... *C12Q 1/701* (2013.01); *C12Q 2600/158* (2013.01)

(58) Field of Classification Search
None
See application file for complete search history.

(56) References Cited

U.S. PATENT DOCUMENTS 9,938,588 B2 *   4/2018   Nix .................. C12Q 1/701

FOREIGN PATENT DOCUMENTS

WO       2015070187 A2     5/2015
WO    WO-2015070187 A2 *  5/2015  ........... C12Q 1/6874

OTHER PUBLICATIONS

Meijer et al. (KP830127 Mar. 2015; KP830129 Mar. 2015) (Year: 2015).*
Lowe et al. (Nucleic Acids Research, 1990, 18(7):1757-1761) (Year: 1990).*
Jenckel et al. (Dissertation, Dec. 2015, Ernst-Moritz-Arndt-Urniresitat-Greifswald, p. 1-141) (Year: 2015).*
Meijer et al. (KP830129 Mar. 2015) (Year: 2015).*
Biswas, K., et al. The nasal microbiota in health and disease: variation within and between subjects. Front Microbiol 2015; 9:134.
Bassis, C. M., et al. The nasal cavity microbiota of healthy adults. Microbiome 2014; 2:27.
Wong, P. H., et al. Isolation of bacterial cerebrospinal fluid culture contaminants at a major military medical center. Diagn Microbiol Infect Dis 2013; 77(4):357-361.
Salter, S. J., et al. Reagent and laboratory contamination can critically impact sequence-based microbiome analyses. BMC Biol 2014; 12:87.
Boysen, M. M., et al. Positive cerebrospinal fluid cultures after normal cell counts are contaminants. J Emerg Med 2009; 37(3):251-256.
Olson, D. A., et al. Analysis of bacterial isolates from cerebrospinal fluid. J Clin Microbiol 1984; 19(2):144-146.
Cosseau, C., et al. Proteobacteria from the human skin microbiota: Species-level diversity and hypotheses. One Health 2016: 2:33-41.
Gao, Z., et al. Molecular analysis of human forearm superficial skin bacterial biota. Proc Natl Acad Sci U S A 2007; 104(8):2927-2932.
Li, W., et al. Human endogenous retrovirus-K contributes to motor neuron disease. Sci Transl Med 2015; 7(307):307ra153.
Bowen, L.N., et al. HIV-associated motor neuron disease: HERV-K activation and response to antiretroviral therapy. Neurology 2016; 87:1756-1762.
Morandi, E., et al. The association between human endogenous retroviruses and multiple sclerosis: A systematic review and meta-analysis. PLoS One 2017; 12:e0172415.
Hohn, O., et al. HERV-K(HML-2), the Best Preserved Family of HERVs: Endogenization, Expression, and Implications in Health and Disease. Front Oncol 2013; 3:246.
Christensen, T. Human endogenous retroviruses in neurologic disease. APMIS 2016; 124:116-126.
Ruggieri, V., et al. Enterovirus D68 infection in a cluster of children with acute flaccid myelitis, Buenos Aires, Argentina, 2016. Eur J Paediatr Neurol 2017; 21(6):884 890.
Engelmann, I., et al. Enterovirus D68 detection in respiratory specimens: Association with severe disease. J Med Virol 2017; 89(7):1201-1207.
Hixon, A. M., et al. A mouse model of paralytic myelitis caused by enterovirus D68. PLoS Pathog 2017; 13(2):e1006199.
Dyda, A., et al. The association between acute flaccid myelitis (AFM) and Enterovirus D68 (EV-D68)—what is the evidence for causation? Eurosurveillance 2018; 23(3):17-00310.
Guerra, J. A., et al. Seroepidemiological and phylogenetic characterization of neurotropic enteroviruses in Ireland, 2005-2014. J Med Virol 2017; 89(9):1550-1558.
Bonwitt, J., et al. Acute Flaccid Myelitis Among Children—Washington, Sep.-Nov. 2016. MMWR Morb Mortal Wkly Rep 2017; 66(31):826-829.
Kreuter, J. D., et al. A fatal central nervous system enterovirus 68 infection. Arch Pathol Lab Med 2011; 135(6):793-796.
Khetsuriani, N., et al. Enterovirus surveillance—United States, 1970-2005. MMWR Surveill Summ 2006; 55(8):1-20.

(Continued)

*Primary Examiner* — Stephanie K Mummert

(57) ABSTRACT

A method of detecting Enterovirus D68 is provided. The method may include adding to a mixture containing the sample from the subject, (a) a first forward primer comprising SEQ ID NO: 1, (b) a second forward primer comprising SEQ ID NO: 2, (c) a third forward primer comprising SEQ ID NO: 3, (d) a first reverse primer comprising SEQ ID NO: 4, and (e) a second reverse primer comprising SEQ ID NO: 5, subjecting the mixture to conditions that allow nucleic acid amplification, and detecting the presence or absence of Enterovirus D68 by analyzing the nucleic acid amplification products. The forward primers may include a first universal tail sequence and reverse primers may include a second universal tail sequence. The nucleic acid amplification products may be sequenced using next-generation sequencing.

6 Claims, 1 Drawing Sheet
Specification includes a Sequence Listing.

(56) References Cited

OTHER PUBLICATIONS

Giombini, E., et al. Enterovirus D68-Associated Acute Flaccid Myelitis in Immunocompromised Woman, Italy. Emerg Infect Dis 2017; 23(10):1690-1693.
European Center for Disease Prevention and Control. Rapid Risk Assessment—Enterovirus detections associated with severe neurological symptoms in children and adults in European countries, Aug. 8, 2016. Stockholm: ECDC; 2016.
Liu, D.. Molecular Detection of Human Viral Pathogens, Chapter 1: Introductory Remarks. CRC Press, Taylor & Francis Group 2011; pp. 1-8.
Varghese, R., et al. Sampling the upper respiratory tract for enteroviral infection is important in the investigation of an acute neurological illness in children. Eur J Paediatr Neurol 2015; 19(4):494-495.
Bale Jr., J. F. Virus and Immune-Mediated Encephalitides: Epidemiology, Diagnosis, Treatment, and Prevention. Pediatr Neurol 2015; 53(1):3-12.
Hixon, A. M., et al. Evaluating treatment efficacy in a mouse model of enterovirus D68 paralytic myelitis. J Infect Dis 2017; 216(10):1245-1253.
Unger, S. A., et al. The respiratory microbiome and respiratory infections. J Infect 2017; 74 Suppl 1:S84-S88.
Huang, W., et al. Whole-Genome Sequence Analysis Reveals the Enterovirus D68 Isolates during the United States 2014 Outbreak Mainly Belong to a Novel Clade. Sci Rep 2015; 5:15223.
Gong, Y. N., et al. Molecular evolution and the global reemergence of enterovirus D68 by genome-wide analysis. Medicine (Baltimore) 2016; 95:e4416.
Ng, T. F., et al. Detection and Genomic Characterization of Enterovirus D68 in Respiratory Samples Isolated in the United States in 2016. Genome Announc 2016; 4(6):e01350-16.
Kuss, S.K., et al. Intestinal microbiota promote enteric virus replication and systemic pathogenesis. Science 2011; 334(6053):249-252.
De Steenhuijsen Piters, W. A., et al. Nasopharyngeal Microbiota, Host Transcriptome, and Disease Severity in Children with Respiratory Syncytial Virus Infection. Am J Respir Crit Care Med 2016; 194(9):1104-1115.
Gonzalez-Hernandez, M. J., et al. Regulation of the human endogenous retrovirus K (HML-2) transcriptome by the HIV-1 Tat protein. J Virol 2014; 88(16):8924-8935.
Granerod, J., et al. Neuroimaging in encephalitis: analysis of imaging findings and interobserver agreement. Clin Radiol 2016; 71(10):1050-1058.
De Bolle, L., et al. Quantitative analysis of human herpesvirus 6 cell tropism. J Med Virol 2005; 75(1):76-85.
Saitoh, A., et al. Acute disseminated encephalomyelitis associated with enteroviral infection. Pediatr Infect Dis J 2004; 23(12):1174-1175.
Wali, R. K., et al. Acute Neurological Illness in a Kidney Transplant Recipient Following Infection With Enterovirus-D68: An Emerging Infection? Am J Transplant 2015; 15(12):3224-3228.
Pillai, S., et al. Confirmed enterovirus encephalitis with associated steroid-responsive acute disseminated encephalomyelitis: an overlapping infection and inflammation syndrome. Eur J Paediatr Neurol 2015; 19(2):266-270.
Britton, P. N., et al. Encephalitis in Australian children: contemporary trends in hospitalisation. Arch Dis Child 2016; 101(1):51-56.
Kim, J. M., et al. Simultaneous presentation of acute disseminated encephalomyelitis (ADEM) and systemic lupus erythematosus (SLE) after enteroviral infection: can ADEM present as the first manifestation of SLE? Lupus 2015; 24(6):633-637.
Wender, M. Acute disseminated encephalomyelitis (ADEM). J Neuroimmunol 2011; 231(1-2):92-99.
Martin, J. A., et al. Outcomes of Colorado children with acute flaccid myelitis at 1 year. Neurology 2017; 89(2):129-137.
Huang, W., et al. Complete Genome Sequences of Nine Enterovirus D68 Strains from Patients of the Lower Hudson Valley, New York, 2016. Genome Announc 2016; 4(6):e01394-16.
Kaida, A., et al. Distinct genetic clades of enterovirus D68 detected in 2010, 2013, and 2015 in Osaka City, Japan. PLoS One 2017; 12(9):e0184335.
Chamberlin, M., et al. New RNA polymerase from *Escherichia coli* infected with bacteriophage T7. Nature 1970; 228:227-231.
Wu, D. Y., et al. The ligation amplification reaction (LAR)-amplification of specific DNA sequences using sequential rounds of template-dependent ligation. Genomics 1989; 4:560-569.
Holland, P. M., et al. Detection of specific polymerase chain reaction product by utilizing the 5'—3' exonuclease activity of Thermus aquaticus DNA polymerase. Proc Natl Acad Sci USA 1991; 88(16):7276-7280.
Divison of Viral Diseases, National Centers for Immunization and Respiratory Diseases, CDC, et al. Notes from the field: acute flaccid myelitis among persons aged ≤21 years—United States, Aug. 1-Nov. 13, 2014. MMWR Morb Mortal Wkly Rep 2015; 63(53):1243-1244.
Pastula, D.M., et al. Acute neurologic illness of unknown etiology in children—Colorado, Aug.-Sep. 2014. MMWR Morb Mortal Wkly Rep 2014; 63(40):901-902.
Sejvar, J.J., et al. Acute flaccid myelitis in the United States, Aug.-Dec. 2014: results of nationwide surveillance. Clin Infect Dis 2016; 63(6):737-745.
Council of State and Territorial Epidemiologists (CSTE). CSTE position statement, 15-ID-01: Standardized case definition for acute flaccid myelitis. pp. 1-6; Retrieved from the internet Sep. 4, 2018 at: http://c.ymcdn.com/sites/www.cste.org/resource/resmgr/2015PS/2015PSFinal/15-ID-01.pdf.
Colman, R.E., et al. Rapid drug susceptibility testing of drug-resistant mycobacterium tuberculosis isolates directly from clinical samples by use of amplicon sequencing: a proof-of-concept study. J Clin Microbiol 2016; 54(8):2058-2067.
Bowers, J.R., et al. KlebSeq, a diagnostic tool for surveillance, detection, and monitoring of klebsiella pneumoniae. J Clin Microbiol 2016; 54(10):2582-2596.
Grice, E. A., et al. The skin microbiome. Nat Rev Microbiol 2011; 9(4):244-253.
Noor, A., et al. Enterovirus Infections. Pediatr Rev 2016; 37(12):505-515.
Nathanson, N., et al. From emergence to eradication: the epidemiology of poliomyelitis deconstructed. Am J Epidemiol 2010; 172(11):1213-1229.
Suresh, S., et al. Non-polio Enterovirus detection with acute flaccid paralysis: A systematic review. J Med Virol 2018; 90(1):3-7.
Wiznitzer, M., et al. Acute flaccid myelitis and enterovirus D68: Deja vu all over again. Neurology 2017; 89(2):112-113.
Tokarz, R., et al. Worldwide emergence of multiple clades of enterovirus 68. J Gen Virol 2012; 93(Pt 9):1952-1958.
Maloney, J. A., et al. MRI findings in children with acute flaccid paralysis and cranial nerve dysfunction occurring during the 2014 enterovirus D68 outbreak. AJNR Am J Neuroradiol 2015; 36(2):245-250.
Greninger, A. L., et al. A novel outbreak enterovirus D68 strain associated with acute flaccid myelitis cases in the USA (2012-14): a retrospective cohort study. Lancet Infect Dis 2015; 15(6):671-682.
Messacar, K., et al. A cluster of acute flaccid paralysis and cranial nerve dysfunction temporally associated with an outbreak of enterovirus D68 in children in Colorado, USA. Lancet 2015; 385(9978):1662-1671.
Aliabadi, N., et al. Enterovirus D68 Infection in Children with Acute Flaccid Myelitis, Colorado, USA, 2014. Emerg Infect Dis 2016; 22(8):1387-1394.
Ayscue, P., et al. Acute flaccid paralysis with anterior myelitis—California, Jun. 2012-Jun. 2014. MMWR Morb Mortal Wkly Rep 2014; 63(40):903-906.
Van Haren, K., et al. Acute Flaccid Myelitis of Unknown Etiology in California, 2012-2015. JAMA 2015; 314(24):2663-2671.
Lang, M., et al. Acute flaccid paralysis following enterovirus D68 associated pneumonia, France, 2014. Euro Surveill 2014; 19(44):1-5.
Cabrerizo, M., et al. First Cases of Severe Flaccid Paralysis Associated with Enterovirus D68 Infection in Spain, 2015-2016. Pediatr Infect Dis J 2017; 36(12):1214-1216.

(56) References Cited

OTHER PUBLICATIONS

Dyrdak, R., et al. Outbreak of enterovirus D68 of the new B3 lineage in Stockholm, Sweden, Aug. to Sep. 2016. Euro Surveill 2016; 21(46).

Chong, P. F., et al. Clinical Features of Acute Flaccid Myelitis Temporally Associated with an Enterovirus D68 Outbreak: Results of a Nationwide Survey of Acute Flaccid Paralysis in Japan, Aug.-Dec. 2015. Clin Infect Dis 2018; 66(5):653-664.

Wang, G., et al. Enterovirus D68 Subclade B3 Strain Circulating and Causing an Outbreak in the United States in 2016. Sci Rep 2017; 7(1):1242.

Knoester, M., et al. Upsurge of Enterovirus D68, the Netherlands, 2016. Emerg Infect Dis 2017; 23(1):140-143.

Iverson, S.A., et al. Notes from the Field: Cluster of Acute Flaccid Myelitis in Five Pediatric Patients—Maricopa County, Arizona, 2016. Morb Mortal Wkly Rep 2017; 66(28):758-760.

Del Gaudio, S., et al. Preamplification procedure for the analysis of ancient DNA samples. Scientific World Journal 2013:734676.

Del Gaudio, S., et al. A preamplification approach to GMO detection in processed foods. Anal Bioanal Chem 2010; 396:2135-2142.

Lal, D., et al. Mapping and Comparing Bacterial Microbiota in the Sinonasal Cavity of Healthy, Allergic Rhinitis, and Chronic Rhinosinusitis Subjects. International Forum of Allergy and Rhinology 2017; 7(6):561-569.

Klindworth, A., et al. Evaluation of general 16S ribosomal RNA gene PCR primers for classical and next-generation sequencing-based diversity studies. Nucleic Acids Res 2013; 41(1):e1.

Caporaso, J. G., et al. QIIME allows analysis of high-throughput community sequencing data. Nat Methods 2010; 7(5):335-336.

Edgar, R. C. Search and clustering orders of magnitude faster than BLAST. Bioinformatics 2010; 26(19):2460-2461.

Caporaso, J. G., et al. PyNAST: a flexible tool for aligning sequences to a template alignment. Bioinformatics 2010; 26(2):266-267.

Desantis, T. Z., et al. Greengenes, a chimera-checked 16S rRNA gene database and workbench compatible with ARB. Appl Environ Microbiol 2006; 72(7):5069-5072.

Haas, B. J., et al. Chimeric 16S rRNA sequence formation and detection in Sanger and 454-pyrosequenced PCR amplicons. Genome Res 2011; 21(3):494-504.

McDonald, D., et al. An improved Greengenes taxonomy with explicit ranks for ecological and evolutionary analyses of bacteria and archaea. ISME J 2012; 6(3):610-618.

Freitas, T. A., et al. Accurate read-based metagenome characterization using a hierarchical suite of unique signatures. Nucleic Acids Res 2015; 43(10):e69.

Segata, N., et al. Metagenomic microbial community profiling using unique clade-specific marker genes. Nat Methods 2012; 9(8):811-814.

Heid, C. A., et al. Real time quantitative PCR. Genome Research 1996; 6(10):986-994.

Ackelsberg, J., et al. Lack of Evidence for Plague or Anthrax on the New York City Subway. Cell Syst 2015; 1(1):4-5.

Afshinnekoo, E., et al. Modern Methods for Delineating Metagenomic Complexity. Cell Syst 2015; 1(1):6-7.

Afshinnekoo, E., et al. Geospatial Resolution of Human and Bacterial Diversity with City-Scale Metagenomics. Cell Syst 2015; 1(1):72-87, 97.

Merchant, S., et al. Unexpected cross-species contamination in genome sequencing projects. PeerJ 2014; 2:e675.

Schmieder, R., et al. Fast identification and removal of sequence contamination from genomic and metagenomic datasets. PLoS One 2011; 6(3):e17288.

Tao, Z. Y., et al. Vector sequence contamination of the Plasmodium vivax sequence database in PlasmoDB and In silico correction of 26 parasite sequences. Parasit Vectors 2015; 8:318.

Li, H., et al. Fast and accurate short read alignment with Burrows-Wheeler transform. Bioinformatics 2009; 25(14):1754-1760.

Langmead, B., et al. Fast gapped-read alignment with Bowtie 2. Nat Methods 2012; 9(4):357-359.

Ondov, B. D., et al. Mash: fast genome and metagenome distance estimation using MinHash. Genome Biol 2016; 17(1):132.

Bowers, J. R., et al. Direct detection of Coccidioides from Arizona soils using CocciENV, a highly sensitive and specific real-time PCR assay. Med Mycol 2018; doi: 10.1093/mmy/myy007. [Epub ahead of print].

Bolger AM, et al. Trimmomatic: a flexible trimmer for Illumina sequence data. Bioinformatics 2014; 30(15):2114-2120.

Milne, I., et al. Using Tablet for visual exploration of second-generation sequencing data. Brief Bioinform 2013; 14(2):193-202.

* cited by examiner

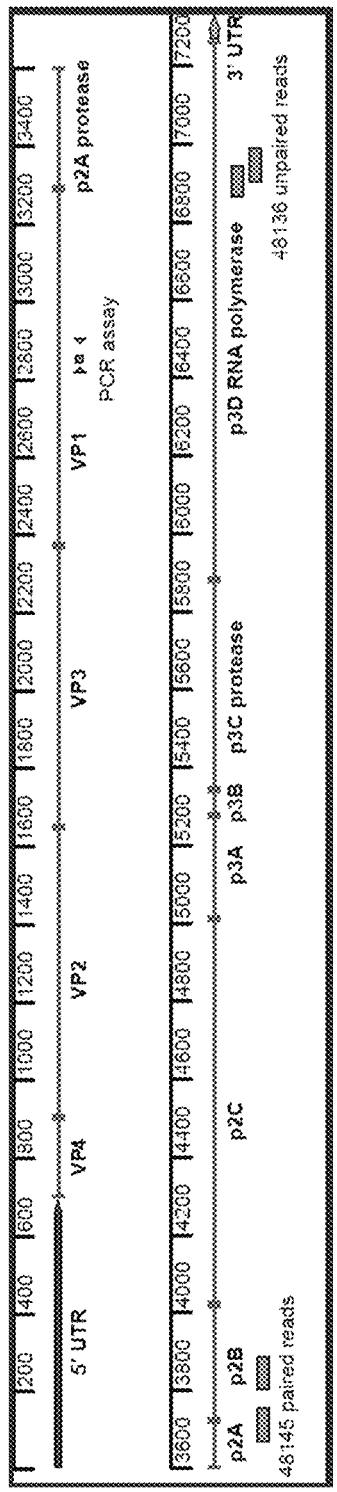

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Primer/Probe

<400> SEQUENCE: 1
crtgggtctt cctgacttra c                                              21

<210> SEQ ID NO 2
<211> LENGTH: 20
<212> TYPE: DNA
<213> ORGANISM: Artificial Sequence
<220> FEATURE:
<223> OTHER INFORMATION: Primer/Probe

<400> SEQUENCE: 2
ayrggccttc ctgacttgac                                                20

<210> SEQ ID NO 3
<211> LENGTH: 21
<212> TYPE: DNA
<213> ORGANISM: Artificial Sequence
<220> FEATURE:
<223> OTHER INFORMATION: Primer/Probe

<400> SEQUENCE: 3
ygtgggtctt cctgacttga c                                              21

<210> SEQ ID NO 4
<211> LENGTH: 20
<212> TYPE: DNA
<213> ORGANISM: Artificial Sequence
<220> FEATURE:
<223> OTHER INFORMATION: Primer/Probe

<400> SEQUENCE: 4
rcctgaytgc cartggaatg                                                20

<210> SEQ ID NO 5
<211> LENGTH: 20
<212> TYPE: DNA
<213> ORGANISM: Artificial Sequence
<220> FEATURE:
<223> OTHER INFORMATION: Primer/Probe

<400> SEQUENCE: 5
gcctgaytgc cartggaayg                                                20

<210> SEQ ID NO 6
<211> LENGTH: 26
<212> TYPE: DNA
<213> ORGANISM: Artificial Sequence
<220> FEATURE:
<223> OTHER INFORMATION: Primer/Probe

<400> SEQUENCE: 6
cargcaatgt ttgtaccbac tggtgc                                         26

<210> SEQ ID NO 7
<211> LENGTH: 26
<212> TYPE: DNA
<213> ORGANISM: Artificial Sequence

```
<220> FEATURE:
<223> OTHER INFORMATION: Primer/Probe

<400> SEQUENCE: 7
caagcaatgt tygtrcccac tggtgc                                       26

<210> SEQ ID NO 8
<211> LENGTH: 38
<212> TYPE: DNA
<213> ORGANISM: Artificial Sequence
<220> FEATURE:
<223> OTHER INFORMATION: Primer/Probe

<400> SEQUENCE: 8
acccaactga atggagccrt gggtcttcct gacttrac                          38

<210> SEQ ID NO 9
<211> LENGTH: 37
<212> TYPE: DNA
<213> ORGANISM: Artificial Sequence
<220> FEATURE:
<223> OTHER INFORMATION: Primer/Probe

<400> SEQUENCE: 9
acccaactga atggagcayr ggccttcctg acttgac                           37

<210> SEQ ID NO 10
<211> LENGTH: 38
<212> TYPE: DNA
<213> ORGANISM: Artificial Sequence
<220> FEATURE:
<223> OTHER INFORMATION: Primer/Probe

<400> SEQUENCE: 10
acccaactga atggagcygt gggtcttcct gacttgac                          38

<210> SEQ ID NO 11
<211> LENGTH: 39
<212> TYPE: DNA
<213> ORGANISM: Artificial Sequence
<220> FEATURE:
<223> OTHER INFORMATION: Primer/Probe

<400> SEQUENCE: 11
acgcacttga cttgtcttcr cctgaytgcc artggaatg                         39

<210> SEQ ID NO 12
<211> LENGTH: 39
<212> TYPE: DNA
<213> ORGANISM: Artificial Sequence
<220> FEATURE:
<223> OTHER INFORMATION: Primer/Probe

<400> SEQUENCE: 12
acgcacttga cttgtcttcg cctgaytgcc artggaayg                         39

<210> SEQ ID NO 13
<211> LENGTH: 34
<212> TYPE: DNA
<213> ORGANISM: Artificial Sequence
<220> FEATURE:
<223> OTHER INFORMATION: Primer/Probe
<220> FEATURE:
<221> NAME/KEY: misc_feature
<222> LOCATION: (26)..(26)
<223> OTHER INFORMATION: n is a, c, g, or t
```

```
<400> SEQUENCE: 13
acccaactga atggagccct acgggnggcw gcag                             34

<210> SEQ ID NO 14
<211> LENGTH: 40
<212> TYPE: DNA
<213> ORGANISM: Artificial Sequence
<220> FEATURE:
<223> OTHER INFORMATION: Primer/Probe

<400> SEQUENCE: 14
acgcacttga cttgtcttcg actachvggg tatctaatcc                       40

<210> SEQ ID NO 15
<211> LENGTH: 17
<212> TYPE: DNA
<213> ORGANISM: Artificial Sequence
<220> FEATURE:
<223> OTHER INFORMATION: Primer/Probe

<400> SEQUENCE: 15
acccaactga atggagc                                                17

<210> SEQ ID NO 16
<211> LENGTH: 19
<212> TYPE: DNA
<213> ORGANISM: Artificial Sequence
<220> FEATURE:
<223> OTHER INFORMATION: Primer/Probe

<400> SEQUENCE: 16
acgcacttga cttgtcttc                                              19
```

METHODS FOR THE DETECTION OF ENTEROVIRUS D68 IN COMPLEX SAMPLES

CROSS-REFERENCE TO RELATED APPLICATIONS

This application claims the benefit of U.S. Provisional Patent Application No. 62/535,813, filed on Jul. 21, 2017, the contents of which is incorporated herein by reference in its entirety.

STATEMENT REGARDING FEDERALLY SPONSORED RESEARCH

This invention was made with governmental support under contract number 200-2016-92313 awarded by the Centers for Disease Control and Prevention (CDC). The United States government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,307 byte ASCII (text) file named "261US_Seq_List" created on Jul. 18, 2018.

FIELD

The present invention relates to the field of detection of Enterovirus species, for example, Enterovirus D68 (EV-D68), which has been implicated in the pathogenesis of acute flaccid myelitis (AFM).

BACKGROUND

The United State has been experiencing a nationwide increase acute flaccid myelitis (AFM) cases. In 2016, the Centers for Disease Control and Prevention (CDC) confirmed 149 cases from 39 states. AFM is a condition that affects the nervous system, specifically the spinal cord, which can result from a variety of causes including viral infections. AFM is characterized by a sudden weakness in one or more arms or legs, along with loss of muscle tone and decreased or absent reflexes. Numbness or other physical symptoms are rare, although some patients may have pain in their arms or legs. In some cases, dysfunction of the nerves controlling the head and neck, resulting in such features as facial weakness, difficulty swallowing, or drooping of the eyes, may accompany the limb weakness.

The 2015 Council of State and Territorial Epidemiologists (CSTE) and CDC case definition for a probable AFM case establishes clinical signs of acute flaccid limb weakness and cerebrospinal fluid (CSF) pleocytosis, i.e., CSF white blood cell (WBC) count greater than (>) 5 per $mm^3$ when corrected for red blood cells. The case definition for a confirmed AFM case includes lesions, demonstrated by magnetic resonance imaging (MRI), restricted primarily to the gray matter of the spinal cord, in addition to acute onset of flaccid limb weakness. After investigations in California and Colorado, the CDC characterized AFM in 2014 as an acute flaccid paralysis (AFP). AFM is distinguishable from other forms of AFP by MRI abnormalities of the gray matter of the anterior and posterior spinal cord segments, involving one or more spinal segments. AFP is a serious illness with unknown cause, and there is still no way of preventing AFP.

Certain viruses (such as nonpoliovirus, enteroviruses, adenoviruses, and West Nile virus) can cause rare cases of AFP, and epidemiological results from the 2014 outbreak investigations indicated that Enterovirus D68 (EV-D68) was temporally associated with AFM. No viral etiology for AFM has been definitively established. Enteroviruses comprise a broad assortment of viruses, causing a diverse array of disease manifestations involving respiratory, skin, neurologic, and gastrointestinal sites, but infections are also frequently asymptomatic.

SUMMARY

A need exists for a rapid molecular assay to diagnose patients with suspected EV-D68 respiratory illness, to aid in AFM diagnosis, and for future EV-D68 surveillance and epidemiology. The present invention is directed to a method of detecting one or more Enterovirus species within a sample from a subject. A method of detecting Enterovirus D68 is provided. The method may include adding to a mixture containing the sample from the subject, (a) a first forward primer comprising SEQ ID NO: 1, (b) a second forward primer comprising SEQ ID NO: 2, (c) a third forward primer comprising SEQ ID NO: 3, (d) a first reverse primer comprising SEQ ID NO: 4, and (e) a second reverse primer comprising SEQ ID NO: 5, subjecting the mixture to conditions that allow nucleic acid amplification, and detecting the presence or absence of Enterovirus D68 by analyzing the nucleic acid amplification products.

In various embodiments, the first forward primer, the second forward primer, and the third forward primer may further include a first universal tail sequence. The first universal tail sequence may comprise SEQ ID NO: 15. The first reverse primer and the second reverse primer may include a second universal tail sequence. The second universal tail sequence may comprise SEQ ID NO: 16. The method may further comprise adding an index to the nucleic acid amplification products using at least one indexing oligonucleotide, and analyzing the nucleic acid amplification products by sequencing the nucleic acid amplification products using next-generation sequencing. The method may comprise adding to the mixture a detectably labeled first probe comprising SEQ ID NO: 6 and a detectably labeled second probe comprising SEQ ID NO: 7, and detecting the detectably labeled first probe and the detectably labeled second probe, thereby detecting the presence of Enterovirus D68 in the subject. In various embodiments, the sample may comprise a nasopharyngeal swab sample.

A method of detecting Enterovirus D68 in a subject may comprise the step of producing an amplicon by amplifying a nucleic acid segment from a sample obtained from the subject with, (a) a first primer comprising SEQ ID NO: 8, (b) a second primer comprising SEQ ID NO: 9, (c) a third primer comprising SEQ ID NO: 10, (d) a fourth primer comprising SEQ ID NO: 11, and (e) a fifth primer comprising SEQ ID NO: 12. The method may include the step of sequencing the amplicon to detect the Enterovirus D68.

In various embodiments, the first primer, the second primer, and the third primer may include a first universal tail sequence, such as SEQ ID NO: 15. The fourth primer and the fifth primer may include a second universal tail sequence, such as SEQ ID NO: 16. The method may comprise adding an index to the amplicon using at least one indexing oligonucleotide. The indexing oligonucleotide may comprise a complementary sequence that recognizes at least one of the first universal tail sequence and the second universal tail sequence. The method may comprise the step of sequencing the amplicon using next-generation sequencing.

A method of detecting Enterovirus D68 in a sample from a subject may comprise the steps of extracting nucleic acids from the sample and subjecting the nucleic acids to a PCR amplification reaction using (a) a first forward primer comprising SEQ ID NO: 1, (b) a second forward primer comprising SEQ ID NO: 2, (c) a third forward primer comprising SEQ ID NO: 3, (d) a first reverse primer comprising SEQ ID NO: 4, and (e) a second reverse primer comprising SEQ ID NO: 5. The method may include the step of analyzing the nucleic acid amplification products resulting from the PCR amplification reaction to detect the Enterovirus D68.

In various embodiments, the first primer, the second primer, and the third primer may further include a first universal tail sequence, such as SEQ ID NO: 15. The fourth primer and the fifth primer may further include a second universal tail sequence, such as SEQ ID NO: 16. The method may comprise the step of adding an index to the nucleic acid amplification products using at least one indexing oligonucleotide. The at least one indexing oligonucleotide may comprise a complementary sequence that recognizes at least one of the first universal tail sequence and the second universal tail sequence. The step of analyzing the nucleic acid amplification products may further comprise sequencing the nucleic acid amplification products using next-generation sequencing.

The method may comprise adding to the PCR amplification reaction a detectably labeled first probe comprising SEQ ID NO: 6 and a detectably labeled second probe comprising SEQ ID NO: 7. The step of analyzing the nucleic acid amplification products may further comprise detecting the detectably labeled first probe and the detectably labeled second probe, thereby detecting the presence of Enterovirus D68 in the subject The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE FIGURES

FIG. 1 shows EV-D68 genome map with locations of the real-time PCR/amplicon sequencing assay and the metagenomic read alignments of two NP swab samples from patients diagnosed with AFM.

DETAILED DESCRIPTION

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

As used herein, "amplification reaction" refers to a method of detecting target nucleic acid by in vitro amplification of DNA or RNA.

As used herein, "polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

The term "primer" refers to DNA oligonucleotides complementary to a region of DNA and serves as the initiation of amplification reaction from the 5' to 3' direction.

The term "primer pair" refers to the forward and reverse primers in an amplification reaction leading to amplification of a double-stranded DNA region of the target.

The term "target" refers to a nucleic acid region bound by a primer pair that is amplified through an amplification reaction. The PCR "product" or "amplicon" is the amplified nucleic acid resulting from PCR of a set of primer pairs.

The term "multiplex amplification reaction" herein refers to the detection of more than one template in a mixture by the addition of more than one set of oligonucleotide primers.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more amplicons.

The term "template" refers to nucleic acid originating from a sample that is analyzed for the presence of one or more markers. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

In some embodiments, the present invention comprises a method of detecting Enterovirus D68 in a subject, comprising the steps of contacting a sample obtained from the subject with, (a) a first forward primer comprising SEQ ID NO: 1, (b) a second forward primer comprising SEQ ID NO: 2, (c) a third forward primer comprising SEQ ID NO: 3, (d) a first reverse primer comprising SEQ ID NO: 4, (e) a second reverse primer comprising SEQ ID NO: 5, (f) a detectably labeled first probe comprising SEQ ID NO: 6, and (g) a detectably labeled second probe comprising SEQ ID NO: 7. The method may further include carrying out real-time PCR; and detecting the detectably labeled first probe and the detectably labeled second probe, thereby detecting the presence of Enterovirus D68 in the subject.

Detection according to some embodiments of the disclosure may comprise contacting the amplified nucleic acid with a probe; and detecting the hybridization of probe with the amplified nucleic acid. Detection may be performed by a variety of methods, such as but not limited to, by a nucleic acid amplification reaction. In some embodiments the amplification reaction maybe an end-point determination or the amplification reaction maybe quantitative. The quantification may be a real-time PCR (RT-PCR) method. In some embodiments, the real-time PCR may be a SYBR® Green Assay or a TAQMAN® Assay. Detection, in various embodiments, maybe performed by hybridization using probes specific to target sequences. According to various embodiments, combinations of amplification and hybridization may be used for detection.

As used herein, "real-time PCR" or "RT-PCR" may refer to the detection and quantitation of a DNA or a surrogate thereof in a sample. In some embodiments, the amplified segment or "amplicon" can be detected in real time using a 5'-nuclease assay, particularly the TaqMan® assay as described by e.g., Holland et al. (Proc. Natl. Acad. Sci. USA 88:7276-7280, 1991); and Heid et al. (Genome Research 6:986-994, 1996). For use herein, a TaqMan® nucleotide sequence to which a TaqMan® probe binds can be designed into the primer portion, or known to be present in DNA of a sample. In some embodiments, the PCR methods use end-point PCR and a positive result is obtained when there is a detectable signal after the PCR is finished. Real-time and end-point PCR methods useful in accordance with the present methods and compositions include, but are not limited to, fluorescence resonance energy transfer (FRET), TAQMAN®, Molecular Beacons, Amplifluor®, Scorpion™, Plexor™, BHQplus™.

Detection method embodiments using a TaqMan® probe sequence comprise combining the test sample with PCR reagents, including a primer set having a forward primer and a reverse primer, a DNA polymerase, and a fluorescent detector oligonucleotide TaqMan® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

As described in greater detail herein, some embodiments of the invention may include amplicon-based sequencing of the one or more markers to make the aforementioned determinations. Some embodiments of the invention include systems and methods of preparing samples for one or more downstream processes that can be used for assessing one or more markers for any of the previously mentioned purposes. Some embodiments of the invention may comprise a universal indexing sequencing strategy for use in downstream sequencing platform processes. By way of example only, some embodiments of the invention comprise a universal indexing sequencing strategy that can be used to amplify multiple genomic regions (e.g., markers, as described below) from a DNA sample simultaneously in a single reaction for the sequencing of one or more amplicons. One or more embodiments of the invention can be used with any desired sequencing platform, such as the ILLUMINA® Next Generation Sequencing (e.g., MiSeq) platform, Life Technologies' Ion Torrent System, or any other sequencing system now known or developed in the future.

Some embodiments may be configured to enable relatively simple, rapid (e.g., microorganism-culture independent), inexpensive, and efficient preparation of samples for use on, in, and/or with downstream sequencing platforms. For example, some embodiments may use a sequence coupled to one or more oligonucleotides/primers (as used herein, oligonucleotides and primers are used interchangeably). More specifically, one or more amplicons per sample can be generated using a hybrid oligonucleotide that is designed for amplification of a marker and incorporation of at least one universal tail sequence into the resulting amplicon. As a result, additional steps that may be conventionally required to prepare samples for sequencing can be limited or removed entirely. Further information regarding the universal tail, amplicon-based sequencing strategy can be found in PCT/US2014/064890, which is hereby incorporated by reference in its entirety for all purposes.

In some embodiments, the methodology may include performing downstream sequencing on one or more amplicons. For example, in order to minimize and/or eliminate the need for cultures of microorganisms or large inputs of nucleic acids, methodologies of the instant invention may include an initial PCR step to create amplicons that correspond to the one or more pre-selected markers. As such, some embodiments require only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of some conventional systems.

Some embodiments of the invention can be used for and/or in complement with high-throughput amplicon sequencing of markers, which can be very useful for a variety of molecular genetic genotyping/predicted-phenotyping applications, including clinical sample analysis. For example, use of the systems and methods of the invention can be employed with sequencing platforms to provide rapid, high-yield sequence data, which can enable the sequencing of multiple markers/amplicons from many samples in a relatively short period of time. Specifically, in some embodiments, amplicons can be selected and PCR reactions can be designed to provide information that can be used to make clinically relevant determinations after sequencing of the amplicons.

In some preferred aspects, the methodology may include creating a series of oligonucleotides designed to provide multiplexed amplification of one or more markers to produce the desired amplicons. In particular, the one or more markers and amplicons thereof can be selected/amplified to provide users with clinically relevant information related to identification of one or more potentially infectious microorganisms and phenotypic and genotypic information about the microorganisms. After production of the amplicons (e.g., via PCR amplification), which may include the universal tail sequences, the method may include processing the resulting amplicons for downstream sequencing and thereafter sequencing the processed amplicons. After processing and analysis of the resulting sequencing data, one of skill in the art can make any necessary determinations regarding the identification of one or more microorganisms that may have been contained within the sample and predicted-phenotypic and/or genotypic information revealed.

Generally, some embodiments of the present invention can be used to detect, identify, assess, sequence, or otherwise evaluate a marker. A marker may be any molecular structure produced by a cell, expressed inside the cell, accessible on the cell surface or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, single-stranded DNA, or complementary sequences thereof. Alternatively, a marker may be represented by a protein sequence. The concept of a marker is not limited to the exact nucleic acid sequence or protein sequence or products thereof; rather it encompasses all molecules that may be detected by a method of assessing the marker. Without being limited by the theory, the detection, identification, assessment, sequencing, or any other evaluation of the marker may encompass an assessment of a change in copy number (e.g., copy number of a gene or other forms of nucleic acid) or in the detection of one or more translocations. Moreover, in some embodiments, the marker may be relevant to a particular phenotype or genotype. By way of example only, in some embodiments, the marker may be related to phenotypes including antibiotic resistance, virulence, or any other phenotype.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

In some aspects, the markers may include one or more sets of amplifiable nucleic acids that can provide diagnostic information about the microorganisms. For example, the markers may include amplifiable nucleic acid sequences that can be used to assess the presence and/or absence of one or more microorganism that may have the potential to cause a diseased state in the subject. In some embodiments, the markers may include amplifiable nucleic acid sequences that can be used to identify one or more of the following exemplary microorganisms and/or viruses: Enterovirus (including but not limited to Enterovirus D68).

In some embodiments, the methods may include the use of one or more than one marker per microorganism. Moreover, in some embodiments, one or more of the microorganisms may not be considered pathogenic to certain subjects, but the methodology employed herein can still rely on detection of pathogenic and non-pathogenic microorganisms for differential diagnoses/diagnostics. In some embodiments, the oligonucleotides (with or without the universal tail sequences detailed herein) listed in TABLE 1 can be used with embodiments of the invention to amplify one or more markers from the microorganisms to provide diagnostic/identification information to the user.

Moreover, in some embodiments, one or more the markers associated with the plurality of microorganisms can be amplified in a multiplex manner. For example, in some aspects, nucleic acids can be obtained from the sample and the oligonucleotides used to amplify one or more of the markers used to identify/diagnose can be added to a single mixture to produce a plurality of amplicons in a single reaction mixture. In other aspects, the oligonucleotides can be added to multiple mixtures to provide for the creation of multiple amplicons in multiple mixtures.

Moreover, in some embodiments, one or more the markers can be amplified in a multiplex manner. For example, in some aspects, nucleic acids can be obtained from the sample and the oligonucleotides used to amplify one or more of the markers used to identify the strain of the microorganism can be added to a single mixture to produce a plurality of amplicons in a single reaction mixture. In other aspects, the oligonucleotides can be added to multiple mixtures to provide for the creation of multiple amplicons in multiple mixtures. In some aspects, amplification of the markers used to identify microorganisms/diagnose an infection can also occur in a multiplex manner such that some or all of the amplicons are generated in a single reaction for a particular sample. In other aspects, amplification of the markers used to identify microorganisms/diagnose an infection can occur in multiple reaction vessels. Overall, as described in greater detail below, regardless of the multiplex nature of some embodiments of the invention, after amplification of the markers, the method may include processing and sequencing the resulting amplicons to provide information related to the identification, characterization, and strain identity of one or more microorganisms that may be present within the sample.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis facilitating genotyping analysis of the samples.

In some forms of PCR assays, quantification of a target in an unknown sample is often required. Such quantification may be determined in reference to the quantity of a control sample. The control sample starting material/template may be co-amplified in the same tube in a multiplex assay or may be amplified in a separate tube. Generally, the control sample contains template at a known concentration. The control sample template may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

Some embodiments of the invention may comprise a multiplex assay. As used herein, the term "multiplex" refers to the production of more than one amplicon, PCR product, PCR fragment, amplification product, etc. in a single reaction vessel. In other words, multiplex is to be construed as the amplification of more than one marker-specific sequences within a PCR reaction or assay within the same PCR assay mixture (e.g., more than one amplicon is produced within a single vessel that contains all of the reagents necessary to perform a PCR reaction). In some embodiments, a step prior to performing the PCR (or RT-PCR, quantitative RT-PCR, etc.) reaction can occur such that sets of primers and/or primers and probes are designed, produced, and optimized within a given set of reaction conditions to ensure proper amplicon production during the performance of the PCR.

The algorithm for Ct values in real-time PCR calculates the cycle at which each PCR amplification reaches a significant threshold. The calculated Ct value is proportional to the number of marker copies present in the sample, and the Ct value is a precise quantitative measurement of the copies of the marker found in any sample. In other words, Ct values represent the presence of respective marker that the primer sets are designed to recognize. If the marker is missing in a sample, there should be no amplification in the real-time PCR reaction.

Alternatively, the Cp value may be utilized. A Cp value represents the cycle at which the increase of fluorescence is highest and where the logarithmic phase of a PCR begins. The LIGHTCYCLER® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments of the invention, the additional organism may be separately cultured after isolation of the sample to provide additional starting materials for downstream analyses. In some embodiments, the sample or biological sample may comprise a direct portion of the additional, non-human organism and the host organism (e.g., a biopsy or sputum sample that contains human cells and bacteria).

With respect to use of the sample or biological sample, embodiments of the claimed methodology provide improvements compared to conventional methodologies. Specifically, conventional methodologies of identifying and characterizing microorganisms include the need for morphological identification and culture growth. As such, conventional methodologies may take an extended period of time to identify the microorganism and may then require further time to identify whether the microorganism possesses and certain markers. Some embodiments of the invention can provide a user with information about any microorganisms present in a sample without the need for additional culturing because of the reliance of nucleic acid amplification and sequencing. In other words, direct extraction of nucleic acids coupled with amplification of the desired markers and downstream sequencing can reduce significantly the time required to obtain diagnostic and strain identifying information.

The invention may further comprise the step of sequencing the amplicon. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfuryrlase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted nucleic acids and/or amplicons are attached to a surface. The fragments/amplicons are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Nucleic acid sequences may be identified by the IUAPC letter code which is as follows: A=Adenine base; C=Cytosine base; G=guanine base; T or U=thymine or uracil base; I=inosine base. M=A or C; R=A or G; W=A or T; S=C or G; Y=C or T; K=G or T; V=A or C or G; H=A or C or T; D=A or G or T; B=C or G or T; N or X=A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, as previously mentioned, the method may include the use of massively parallel sequencing, as detailed in U.S. Pat. Nos. 8,431,348 and 7,754,429, which are hereby incorporated by reference in their entirety.

Some embodiments of the invention comprise multiple steps and/or processes that are carried out to execute the universal tail indexing strategy to prepare amplicons corresponding to desired markers for sequencing. In some embodiments, one or more makers for a given sample or template can be selected, as described above. Some embodiments of the invention can be used in conjunction with an analysis of one or more markers (e.g., genes/alleles) associated with a particular phenotype (e.g., virulence).

After selection of the markers, marker-specific primers/oligonucleotides can be designed for the amplification of the markers to produce the desired amplicons, as detailed above. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 100 bp, 150 bp, 200 bp, 250 bp, 300 bp, 350 bp, 400 bp, 450 bp, 500 bp, 1,000 bp, or any size amplicon greater in size or therebetween.

As previously mentioned, some embodiments of the invention may include a multiplex PCR reaction. For example, marker-specific primers can be designed for multiple markers or multiple regions of the same marker such that multiple amplicons of between about 50 bp and 1,000 bp are being produced within a single PCR reaction vessel. In other words, the forward and reverse primers can be designed to function within a given set of temperature parameters such that more than one amplicon can be successfully amplified from a given template within a single PCR reaction mixture. As such, multiple amplicons can be prepared using the universal tail indexing strategy for sequencing preparation.

In some embodiments, the forward and reverse primers that have been designed for each of the markers can be modified to include a universal tail. For example, the universal tail sequences can be relatively or completely unique sequences of nucleotides that are coupled to the 5' ends of some or all of the forward and reverse marker-specific primers. In some aspects, the universal tail sequences can be selected such that there is little to no overlap in sequence between portions of the markers that are being amplified and the universal tail sequences. Moreover, the universal tail sequences can comprise a length between ten and twenty nucleotides in length. In some embodiments, the universal tail sequences can be any other length, as desired by the user to meet the needs and requirements of the reaction. As such, the universal tail sequences can exhibit a relatively negligible impact on binding of the forward and reverse marker-specific primers to the template sequence to enable amplification. Moreover, as a result of being included on the 5' end of the forward and reverse marker-specific primers, the universal tail sequences will form a portion of the resulting amplicons. In addition, in some aspects of the invention, the sequences selected for the universal tail sequences can be at least partially correlated with the chemical composition of the template nucleic acids. For example, in some aspects, the sequences selected for the universal tail sequences can be at least partially correlated with the G-C content of the organism from which the template is isolated.

In some aspects, some or all of the universal tail sequences can be at least partially unique. In some embodiments, each of the 5' ends of all of the forward marker-specific primers within a given PCR assay mixture can comprise the same or a similar universal tail sequence (e.g., a first universal tail sequence or UT1). Similarly, each of the 5' ends of all of the reverse marker-specific primers within the same PCR assay mixture can comprise a second universal tail sequence (UT2) that differs from the first universal tail sequence. As such, each respective sample from which a template sequence is used in the multiplex PCR assay will have two unique universal tail sequences. Accordingly, each forward and reverse marker-specific primer within a multiplex PCR mixture will include a unique universal tail sequence. For example, if the PCR includes 35 different samples, 35 universal tail sequences can be employed for the forward primers in each of the 35 unique reactions (i.e., not including technical replicates) and 35 universal tail sequences can be employed for the reverse primers in each of the 35 unique reactions (i.e., not including technical replicates). Overall, the forward and reverse marker-specific primers that each comprise the universal tail sequences can comprise a generally short length (e.g., 25-50 bp), which can facilitate simultaneous amplification of multiple targets in a single reaction.

In addition, some embodiments of the invention may comprise performing quantitative PCR to optimize the multiplex PCR assay. For example, after design of the forward and reverse marker-specific primers that each include a universal tail sequence, the contemplated multiplex PCR assays can be performed using quantitative PCR (e.g., using DNA as a template) to assess relative quantities of the amplicons produced. Accordingly, the sequence coverage of each amplicon is considered to be equal if the quantities of the amplicons produced by the multiplex quantitative PCR appear to be equal. If the quantities of the amplicons produced by the multiplex quantitative PCR do not appear to be equal, the forward and/or reverse marker-specific primers can be altered and re-optimized until adequate quantities of amplicons are produced.

After design and adequate optimization of the multiplex PCR assay comprising multiple forward and reverse marker-specific primers that each includes universal tail sequences, the multiplex PCR can be performed to obtain the amplicons associated with the above-described markers. In some embodiments, template that has been previously isolated from a sample can be used for the amplification of the amplicons. In some aspects, multiple PCR reaction replicates can be performed for each sample template and one or more control templates.

In some embodiments, after successful production of the amplicons during the multiplex PCR assay, the resulting amplicons can be further processed to provide sequencing-ready amplicons. For example, some embodiments of the invention may comprise an indexing extension step. In some aspects, the indexing extension step may comprise extending the optimized multiplex amplicons using a set of indexing and common primers that recognize the respective universal tail sequences used for the particular group of amplicons in a minimal cycle PCR assay (e.g., 5-10 total cycles). In particular, each multiplex set of amplicons to be sequenced can be extended with a different set of index oligonucleotides and common oligonucleotides that recognize UT1 and UT2, respectively. In some aspects, the index sequence of the index oligonucleotides can be custom designed to allow for the selection of an index sequence from potentially thousands of different index sequences.

After this step, the resulting products include a set of amplicons for each sample/template that comprise the same index and any necessary sequences that may be required for a particular sequencing platform (e.g., platform sequences associated with the ILLUMINA® Next Generation sequencing platform). Thereafter, the resulting extension-reaction products can be quantified, pooled, and sequenced using a desired platform. In some aspects, the inclusion of the universal tail sequences on the index and common primers can coincide with the use of genomic and index read primers in the mixture of sequencing primer reagents. For example, some embodiments of the invention are capable of pooling multiple amplicons with multiple indices in a single sequencing run to provide 40,000×-95,000× coverage across the amplicons. In other embodiments, the systems and methods associated with the invention can be configured to provide any level of sequencing coverage that is desirable to the user (e.g., higher or lower that the coverage levels discussed above). In some embodiments, after sequencing and generation of the sequence data, the resulting data can be demultiplexed and the sequence files can be aligned to the appropriate references sequences for subsequent sequence analyses.

Some embodiments of the invention may comprise other applications. For example, some embodiments comprise an application of the universal tail sequences that could be used to detect clinically relevant RNA transcripts in a multiplex fashion. For example, RNA can be extracted from a sample, converted to cDNA using techniques known in the art, and the cDNA can function as the template for additional processes (e.g., multiplex PCR assays and subsequent sequencing). In some aspects, the amplicons resulting from the multiplex PCR reaction can be sequenced, in a manner as previously mentioned, and the resulting sequences can be aligned. As a result, differential numbers of sequence reads generated by the sequencing process (i.e., when aligned to the amplicon reference sequences), can provide data regarding the different copy numbers in the original RNA sample. As a result of this process, clinicians can gain an insight into the actual expression of a gene that is present. Specifically, virulence or resistance markers may display differential expression in a clinical sample. As such, understanding differential expression of these markers could be clinically relevant. Moreover, some embodiments could also be used to characterize population diversity using a relatively small set of markers from a very large number of samples, even within a single sample, which can enhance forensic applications.

Some embodiments of the invention comprise the use of PCR before sequencing such that only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of these systems. Moreover, the inclusion of non-desirable template materials can also interfere in one or more downstream processes in conventional systems and methods. For example, if an investigation is being conducted that focuses on one or more organisms that may be associated with another organism (e.g., bacteria associated with a human); the sampling of the target organism may result in template contamination from the host organism.

In particular, in some aspects, obtaining samples of pathogenic or commensal bacteria from, on, or within a human may also result in the collection of human tissue. As such, when isolating the template, human nucleic acids may contaminate the bacterial template. Some embodiments of the invention are configured such that the contaminating template (e.g., from a human) would not interfere with downstream processes, including sequencing. For example, some embodiments of the invention operate such that only a limited amount of starting template (e.g., 500 femtograms or greater) can be used. Moreover, some embodiments are also configured such that the starting material (e.g., template contaminated with foreign nucleic acids) can still produce the required amplicons for sequencing in the presence of more than a 1,000-fold excess of contaminating template with no discernible inhibition of the multiplex PCR.

In certain aspects, the present invention provides an assay that works with as little as about 1 pg, about 900 fg, about 800 fg, about 700 fg, about 600 fg, about 500 fg, about 400 fg, about 300 fg, about 200 fg, or about 100 fg of genomic DNA.

The following examples are given for purely illustrative and non-limiting purposes of the present invention.

Examples

In 2016, physicians in Phoenix, Ariz., USA, noted a cluster of eleven children with symptoms consistent with AFM. A study comprising metagenomic, microbiomic, and targeted analyses was conducted on clinical samples from that outbreak to identify possible etiologic causes of AFM and related neurologic disease. Based on medical chart abstraction and review of the MRI images, a CDC neurology subject matter expert verified four confirmed cases of AFM according to the 2015 CDC case definition, and one probable case. Initial differential diagnoses included transverse myelitis and AFM. As part of the outbreak investigation, cerebrospinal fluid (CSF) samples were collected from all patients between one and thirty-two days from onset of focal limb weakness, and nasopharyngeal (NP) swabs were collected from six of the eleven patients one to fourteen days following onset of illness. Patient sample and testing information is included in TABLES 2 and 3. Chart reviews and patient interviews were conducted during the course of this study, and samples were de-identified and coded prior to off-site genomic analyses; therefore all molecular analyses were blinded.

As shown in TABLE 2, onset dates for the four confirmed cases (Patients 1-4) occurred during Aug. 19, 2016 to Sep. 15, 2016. The four patients had preceding respiratory (three patients) or gastrointestinal (GI) illness (one patient), with onset dates during Aug. 14, 2016 to Sep. 13, 2016. The patients' respiratory or gastrointestinal illness began a median of 2 days (range: 2-5 days) before onset of focal limb weakness; and three patients experienced tactile or measured fever preceding onset of neurologic symptoms. Among patients with confirmed cases, focal limb weakness was present in a single limb (one case), three limbs (two cases), and four limbs (one case). Two patients with confirmed cases and one patient with a probable case had a prior medical history of asthma, and a third patient with a confirmed case reported a family history of asthma. The investigation team conducted hypothesis-generating interviews with all confirmed AFM patients and their proxies. Three of the four patients with confirmed cases were residents of Maricopa County, Ariz. and no epidemiologic links were detected among the four patients. None of the patients had traveled to an area with ongoing Zika virus transmission in the month prior to symptom onset.

To determine if these cases were associated with EV-D68, multiple genomic analyses were performed on nasopharyngeal swabs (if available) and CSF material from the patients, including real-time PCR and amplicon sequencing targeting the EV-D68 VP1 gene, and unbiased microbiome sequencing (i.e., 16S rRNA gene and DNA and RNA shotgun metagenomic sequencing).

Methods

DNA was extracted from 200-400 µL of each patient sample, i.e., NP swab samples and CSF samples, dependent on total volume, with the exception of one sample that contained enough volume for RNA extraction only. DNA was extracted with the DNeasy Blood and Tissue Kit (Qiagen) using the gram-positive protocol in the supplied handbook with some modifications. Initial lysis with enzymatic lysis buffer was extended to 60 minutes at 37° C., and secondary lysis with buffer AL and proteinase K at 56° C. to 30 minutes. RNA was extracted from 100-400 µL of specimen with the High Pure Viral RNA kit (Roche). The extracted DNA and/or RNA was amplified by PCR and prepared for sequencing as described herein.

Real-Time PCR and Targeted Amplicon Sequencing

EV-D68 VP-1 sequences were collected from NCBI's nucleotide database for years 2014 through 2016. Sequences were aligned in SeqMan (DNAStar, Madison, Wis.) to identify conserved regions for primer design, and assays were designed with guidance from RealTimeDesign™ (Biosearch Technologies, Petaluma, Calif.). Each primer and probe was run through Basic Local Alignment Search Tool (BLAST®, National Center for Biotechnology Information, U.S. Laboratory of Medicine, Bethesda, Md.), to check for cross-reactivity to other relevant targets or species, including human. As disclosed herein, the EV-D68 amplicon sequencing assays target a 94 bp region of the VP1 gene of Enterovirus D68. The EV-D68 assay, listed in TABLE 1 and mapped in FIG. 1, results in a 94 bp amplicon. In various embodiments, the EV-D68 real-time PCR assay comprises three forward primers (SEQ ID NOS: 1, 2 and 3), two reverse primers (SEQ ID NOS: 4 and 5), and two probes (SEQ ID NOS: 6 and 7). In various embodiments, the EV-D68 amplicon sequencing assay comprises five amplicon sequencing primers (SEQ ID NOS: 8-12), and may further include indexing primers and sequencing primers. In various embodiments, the 16s amplicon sequencing assay comprises two amplicon sequencing primers (SEQ ID NOS: 13 and 14), and may further include indexing primers and sequencing primers.

First-strand cDNA synthesis of the total RNA was performed with the High Capacity cDNA Reverse Transcription Kit (ThermoFisher Scientific). Preamplification may be used to increase the sensitivity of the subsequent steps, including RT-PCR and/or the amplicon sequencing. Preamplification, which has been shown to greatly increase sensitivity in complex samples, was performed using the Taqman PreAmp Master Mix (ThermoFisher Scientific) with the EV-D68 primers (SEQ ID NOS: 1-5 from TABLE 1) at a final concentration of 5-10 nM. The material resulting from the preamplification step, i.e., the pre-amplified template, was then used for each of the methods, RT-PCR and amplicon sequencing.

Real-time PCR was run on the 7900HT (ThermoFisher Scientific) in 10 µL reactions containing 5 µL PerfeCTa FastMix II, 400-600 nM each primer (SEQ ID NOS: 1-5 from TABLE 1), 200 nM each probe (SEQ ID NOS: 6 and 7 from TABLE 1), and 4 µL pre-amplified template, with denaturation 95° C. for 3 min and 40 cycles of 95° C. for 15 s, 60° C. for 1 min. Results of the real-time PCR are shown in TABLES 2 and 3 for each of the NP swab samples and CSF swab samples (see rows labeled "EV-D68 Taqman Ct").

For the targeted amplicon sequencing method, amplicon library preparation was performed using the universal tail indexing strategy, i.e., using primers having universal tails. The amplicon library preparation comprises two PCR steps, a gene-specific multiplex PCR and an index extension PCR.

First PCR: In gene-specific multiplex PCR reactions, the target amplicons are synthesized with a universal tail sequence added to the amplicons. Each primer includes a gene-specific sequence and a universal tail sequence, the universal tail sequences are underlined in TABLE 1. The forward primers have a first universal tail sequence, and the reverse primers have a second universal tail sequence, with the second universal tail sequence being different than the first universal tail sequence.

For the EV-D68 assay, the initial gene-specific PCR comprised 12 µL 2× Kapa 2G Fast Multiplex Mastermix (Kapa Biosystems), 10 µL primer mix, including SEQ ID NOS: 8-12 from TABLE 1, yielding a final PCR concentration of 200 nM each, and 2 µL DNA template from each sample, and was denatured at 95° C. for 3 min, cycled 20 times at 95° C. 15 s, 60° C. 30 s, 72° C. 1 min 30 s, with final extension 72° C. 1 min. Each primer included a gene-specific sequence and a universal tail sequence (underlined in TABLE 1). The forward primers (SEQ ID NOS: 8-10) included a first universal tail sequence (SEQ ID NO: 15), and the reverse primers (SEQ ID NOS: 11 and 12) included a second universal tail sequence (SEQ ID NO: 16). The amplification of the target results in the production of amplicons that comprise the first and second universal tail sequences integrated therein. After production of the amplicons during the multiplex PCR assay, the resulting amplicons can be further processed an indexing extension step to provide sequencing-ready amplicons.

Second PCR: The indexing extension PCR adds a specific index sequence to the amplicons using the universal tail sequences on either end of the amplicon. Stated differently, the amplicons are extended using platform-specific primers that recognize at least one of UT1 and UT2 for adding the indexes to each amplicon. The index is unique for each sample, such that the indexing primer includes a sample-specific index sequence and a common universal tail complement sequence. Thus, the number of different indexing primers used in the second PCR depends on the number of unique samples being processed in the same PCR. Each indexing primer comprises a complementary sequence that recognizes at least one of the first universal tail sequence and the second universal tail sequence that has been previously integrated within the amplicons. At the end of the index extension PCR there is a sequencer-ready amplicon library. The samples can be pooled for sequencing using a desired platform during a single sequencing run and distinguished based on the index sequence during analysis of the data. The inclusion of the universal tail sequences on the index and common primers may coincide with the use of genomic and index read primers in the mixture of sequencing primer reagents. After sequencing, the resulting data can be de-multiplexed and the sequence files can be aligned to a reference sequence (e.g., a wild type sequence and/or other alleles for each of the respective markers) for subsequent sequence analyses. As a result, the aligned sequences can be analyzed for the presence or absence of markers, variant signatures associated with the markers, differential marker presence in the sample, which includes the capability of analyzing gene expression, and an estimate of allele frequencies of various alleles of the markers in the pooled samples.

For the EV-D68 assay, the second PCR, using the universal tail-specific primers, added Illumina's sample-specific index and sequencing adapters. This PCR comprised 12.5 µL 2×KAPA HiFi HotStart Ready Mix (Roche), universally tailed forward and reverse primers x at 400 nM each, and 10.5 µL cleaned gene-specific PCR product for a final volume of 25 µL, and was denatured at 98° C. 2 min, cycled 6 to 12 times at 98° C. 30 s, 65° C. 20 s, 72° C. 30 s, with final extension 72° C. 5 min. Final PCR products were cleaned with 1× Agencourt AMPure XP beads (Beckman Coulter). Amplicon libraries from individual samples were quantified by qPCR using Kapa Library Quantification Kit (Kapa Biosystems). By adding sample specific index sequences to the amplicons, pools of several samples are made for sequencing. Samples were then pooled in equimolar concentration for sequencing. The amplicons were sequenced by next-generation sequencing on the Illumina® MiSeq platform with 2×250 bp version 2 kit. The sequencing read counts for each patient sample are shown in TABLES 2 and 3 (see rows labeled "EV-D68 amplicon read count").

As discussed, some embodiments of the invention comprise multiple steps and/or processes that are carried out to execute the universal tail indexing strategy to prepare amplicons for sequencing. By decoupling the marker-specific amplification from the addition of the indexes or indices, the marker-specific primers can be shorter and less prone to interactions with other primers, which can facilitate a true multiplex PCR reaction. As such, efficient amplification of multiple targets from very low quality and quantity DNA samples is enabled by this feature, which can be important for clinical and forensic samples.

16S Microbiome Library Preparation, Sequencing, and Analysis

The 16S ribosomal RNA genes in each metagenomic sample were amplified by PCR and prepared for sequencing using the universal tail indexing strategy.

First PCR: For the 16S assay, the first PCR using the primer pair S-D-Bact-0341-b-S-17 and S-D-Bact-0785-a-A-21 with universal tail sequences (see SEQ ID NOS: 13 and 14 in TABLE 1) resulted in an amplicon of 481 bp that spans the V3 and V4 regions of the 16S gene. Amplification was performed in a 25 µl reaction volume containing 12.5 µl Q5 Hot Start High-Fidelity 2× Master Mix (New England Biolabs Inc.), 500 nM/primer (SEQ ID NOS: 13 and 14), and 5-10 µl of DNA using thermal conditions previously described. Amplicons were purified using the Agencourt AMPure XP beads (Beckman Coulter) following the manufacturer's protocol. To separate the bacterial 16S amplicon from the human mitochondrial amplicon, the purified samples were processed through the BluePippin DNA Size Selection System (Sage Science). Briefly, 30 µl of the purified sample was mixed with 10 µl of the internal standard and electrophoresed on a 1.5% pre-cast agarose gel cassette. After separation, eluted samples were removed from the cassettes and indexed by PCR.

Second PCR: For the 16S assay, the index PCR comprised 12.5 µl of KAPA HiFi HotStart ReadyMix (Roche), 400 nM of each indexing primer specific to each universal tail, and 10 µl of BluePippin-purified amplicons in a final reaction volume of 25 µl. Index PCR thermal conditions were: 98° C. for 2 min; 10 cycles of 98° C. for 30 sec, 65° C. for 20 sec, 72° C. for 30 sec, and a final hold of 72° C. for 5 min Indexed libraries were purified with Agencourt AMPure XP beads and quantified using KAPA Library Quantification Kit (Roche) and pooled at equimolar concentrations Amplicons were sequenced at 2×300 on a MiSeq with TruSeq v3 chemistry (Illumina, Inc.). Amplicon read data were deposited in NCBI's SRA under BioProject X.

Bacterial community content and diversity were studied via 16S gene sequence analysis with QIIME, using uclust to pick operational taxonomic units (OTUs), PyNAST to align reads to the Greengenes 16S gene database version 13_8, ChimeraSlayer to detect and filter chimera sequences, and the Greengenes taxonomic classification system to assign taxonomy. OTUs that made up <1% of a sample's population were not included in the final composition results. A DNA extraction blank and a 16S PCR reagent blank were included in the sample preparation and analysis.

DNA and RNA Metagenomic Library Preparation, Sequencing, and Analysis.

Total RNA was subjected to DNase I treatment and concentration using RNA Clean and Concentrator-5 (Zymo Research), then amplified using the SeqPlex RNA Amplification Kit (Sigma-Aldrich) Amplified cDNA was checked for quality and size by Bioanalyzer (Agilent Genomics). Total DNA was subject to fragmentation using a Q800R2 Sonicator (QSonica). Metagenomic sequence libraries were prepared for sequencing and quantified using KAPA Hyper Prep Kit and KAPA Library Quantification Kit (KAPA Biosystems). Libraries were sequenced on the HiSeq 2500 at 2×100 using TruSeq v3 chemistry (Illumina, Inc.).

TABLE 1 shows the primers and probes for a real-time PCR assay targeting the VP1 gene of Enterovirus D68. The EV-D68 amplicon sequencing assays target a 94 bp region of the VP1 gene of Enterovirus D68. In TABLE 1, the assay having a nucleic acid sequence comprising SEQ ID NOS: 1-3, for example, comprise a forward primers, SEQ ID NOS: 4 and 5 comprise reverse primers, and SEQ ID NOS: 6 and 7 comprise probes, each for a real-time PCR assay for detecting EV-D68. SEQ ID NOS: 8-12 comprise primers for an amplicon sequencing assay for detecting EV-D68. SEQ ID NOS: 14 and 15 comprise primers for an amplicon sequencing assay for detecting bacteria.

TABLE 1

| Primers and probes for real-time PCR and amplicon sequencing assays | | | |
|---|---|---|---|
| Assay component | Name | Sequence | SEQ ID NO: |
| RT-PCR primer | EVD68_F1 | CRTGGGTCTTCCTGACTTRAC | 1 |
| RT-PCR primer | EVD68_F2 | AYRGGCCTTCCTGACTTGAC | 2 |
| RT-PCR primer | EVD68_F3 | YGTGGGTCTTCCTGACTTGAC | 3 |
| RT-PCR primer | EVD68_R1 | RCCTGAYTGCCARTGGAATG | 4 |
| RT-PCR primer | EVD68_R2 | GCCTGAYTGCCARTGGAAYG | 5 |
| RT-PCR probe (FAM-BHQ) | EVD68_FB1 | 6FAM-CARGCAATGTTTGTACCBACTGGTGC-BHQ | 6 |
| RT-PCR probe (FAM-BHQ) | EVD68_FB2 | 6FAM-CAAGCAATGTTYGTRCCCACTGGTGC-BHQ | 7 |
| Amplicon sequencing primer | EVD68-UT_F1 | <u>ACCCAACTGAATGGAGC</u>CRTGGGTCTTCCTGACTTRAC | 8 |
| Amplicon sequencing primer | EVD68-UT_F2 | <u>ACCCAACTGAATGGAGC</u>AYRGGCCTTCCTGACTTGAC | 9 |
| Amplicon sequencing primer | EVD68-UT_F3 | <u>ACCCAACTGAATGGAGC</u>YGTGGGTCTTCCTGACTTGAC | 10 |
| Amplicon sequencing primer | EVD68-UT_R1 | <u>ACGCACTTGACTTGTCTTC</u>RCCTGAYTGCCARTGGAATG | 11 |
| Amplicon sequencing primer | EVD68-UT_R2 | <u>ACGCACTTGACTTGTCTTC</u>GCCTGAYTGCCARTGGAAYG | 12 |
| 16S amplicon sequencing primer | UT1-S-D-Bact-0341-b-S-17 | <u>ACCCAACTGAATGGAGC</u>CCTACGGGNGGCWGCAG | 13 |
| 16S amplicon sequencing primer | UT2-S-D-BACT-0785-a-A-21 | <u>ACGCACTTGACTTGTCTTC</u>GACTACHVGGGTATCTAATCC | 14 |
| Universal tail | UT1 | <u>ACCCAACTGAATGGAGC</u> | 15 |
| Universal tail | UT2 | <u>ACGCACTTGACTTGTCTTC</u> | 16 |

In TABLE 1, the universal tails, which are added to the primers for amplicon sequencing, are underlined. Universal tail sequences are ACCCAACTGAATGGAGC (SEQ ID NO: 15) for forward read and ACGCACTTGACTTGTCTTC (SEQ ID NO: 16) for reverse read. The universal tail sequences (underlined) precede the assay-specific primer sequence (not underlined), for example, in SEQ ID NOS: 8, 9, 10, 11 and 12.

Metagenomic Analysis

Three metagenomic analysis tools, GOTTCHA, MetaPhlAn, and MetaSeQ (MTS), were employed for thorough and comparative taxonomic classification of reads from each sample, in order to address the major challenges that arise during taxonomic classification of relatively short high throughput sequencing (HTS) reads, e.g. the significant rates of taxonomic misclassification that arise due to the inevitable genomic similarities among organisms and the inaccuracies in publicly available genomic reference databases, which have been repeatedly shown to contain taxonomically misclassified or contaminant sequences. GOTTCHA minimizes false positive hits and gives accurate taxonomic abundances by providing a "unique" reference database in which only sequences that are unique to a taxonomic group are included, and uses the Burrows-Wheeler Aligner (BWA) (version 0.7.12-r1044 in this study) for alignment. The prokaryotic and viral database versions used in GOTTCHA were v20120316 and v20141222 respectively, and default parameters selected for analysis.

MetaPhlAn preselects a significantly reduced marker library from a reference database by identifying coding sequences that are representative of a given clade or operational taxonomic unit. This reduced reference database obviates pre-processing of sample sequence data and generates only high confidence hits. For MetaPhlAn analysis, default parameters were selected.

MetaSeQ (MTS) was designed to address the extreme computational expense of sequence read alignment to reference databases and false positive potential. For MTS, most human sequence data were computationally subtracted (allowing two mismatches per read). The remaining paired-end sequence reads from each sample were decoupled to ignore pairing information. Reads were then segmented into non-overlapping fragments of 45 nucleotides, and aligned to a local copy of NCBI's GenBank database (accessed Feb. 9, 2017). MTS uses a custom implementation of bowtie's alignment algorithm, which aligns reads while eschewing identification of where and how many times a given read aligns within a given species' genome, providing for a significantly faster first hit query within all reference sequences of a given species. The resulting alignment speedup (up to 1,000×) using MTS allows identification of all species (as per NCBI's TaxID identifier) to which any given read aligns. Only reads that unambiguously align to one and only one species (signature hits) were counted in the taxonomic composition of a sample, thereby significantly reducing false positive hits associated with spurious multi-species read alignments. Lastly, MTS post-filtering of alignments was carried out using a modified MinHash (MASH) procedure, which uses short n-mers to generate pairwise distances between all reference sequences in a taxonomic unit, thereby identifying sequences potentially misclassified in Genbank. For all metagenomic analyses, background results from a blank were subtracted from the sample data where appropriate.

DNA and RNA Metagenomic Library Preparation, Sequencing, and Analysis

Amplicon and metagenomic sequencing results were analyzed using an automated bioinformatics tool referred to as the amplicon sequencing analysis pipeline (ASAP). Using the ASAP bioinformatics method, amplicon or metagenomic sequence reads were first trimmed of adapter and read-through sequences with Trimmomatic, and mapped to a reference sequence with bowtie2 Amplicon sequence was mapped to the PCR amplicon region of a 2016 EV-D68 VP1 gene from a recent whole genome deposition, Genbank accession no. KY385890. Metagenomic data were mapped to the EV-D68 whole genome KY385890 and multiple HERV-K sequences to account for genomic diversity, Genbank accession nos. AY037928, JN675041, JN675026, JN675029, JN675039, JN675061, JN675051, JN675050, JN675052, JN675082, and JN675063. Tablet was used to verify results. Amplicon consensus sequences from this study were deposited under BioProject PRJNA377726.

Results

CSF was collected from all eleven patients. With regards to the four patients (Patients 1-4) with confirmed AFM, the median CSF white blood cell count was 132.5 per $mm^3$ (range: 50-207). Initial viral testing of Patients 1-4 at the hospital included CSF reverse transcription PCR assays for enterovirus (three patients) and West Nile virus (WNV) (two patients), PCR assay for herpes simplex virus (two patients), and enzyme immunoassay to detect immunoglobulin M (IgM) or immunoglobulin G (IgG) for WNV (three patients), all results of which were negative. All CSF samples were negative on amplicon sequencing assay using primers based on the 2014-circulating EV-D68 virus.

Stool samples were collected for Patients 2 and 3 at the time of initial evaluation and were negative on viral culture. One available sample and three additional samples, collected 28, 47, and 63 days, respectively, after onset of focal limb weakness, were sent to the CDC for four enterovirus/parechovirus RT-PCR assays. Patients 1, 2, and 3 were negative for enterovirus/parechovirus (see TABLE 2). A stool sample, collected at day 28 from Patient 4 who did not have an NP swab available, was positive for coxsackievirus A10 (see TABLE 2).

TABLE 2 illustrates a clinical data summary of confirmed and probable cases of acute flaccid myelitis in five patients. Patients are identified by numerals 1, 2, 3, 4, and 5. Patients 1, 2, 3, and 4 were identified as meeting the definition for a confirmed AFM case. Patient 5 was identified as meeting the definition for a probable AFM case. In TABLE 2, a single asterisk (*) indicates fever was reported by the parent who detected the fever. i.e., the patient felt warm to the touch. Double asterisks (**) indicates a T2 weighted MRI image.

TABLE 3 illustrates a clinical data summary of the remaining six patients from the initially reported cluster of 11 potential cases of acute flaccid myelitis that were tested concurrently with Patients 1-5 from TABLE 2. Patients in TABLE 3 are identified by numerals 6, 7, 8, 9, 10 and 11.

TABLE 2

| | Patient 1 | Patient 2 | Patient 3 | Patient 4 | Patient 5 |
|---|---|---|---|---|---|
| | | | Results for Patients 1-5 | | |
| AFM Case status | Confirmed | Confirmed | Confirmed | Confirmed | Probable |
| Age at onset, gender | 3.5 yrs, male | 10 yrs, female | 4 yrs, female | 9 yrs, female | 12 yrs, female |
| Onset date of focal limb weakness | Aug. 23, 2016 | Aug. 19, 2016 | Sep. 15, 2016 | Sep. 8, 2016 | Aug. 27, 2016 |

TABLE 2-continued

Results for Patients 1-5

|  | Patient 1 | Patient 2 | Patient 3 | Patient 4 | Patient 5 |
|---|---|---|---|---|---|
| Onset date of preceding respiratory or gastrointestinal illness | Aug. 21, 2016 (respiratory) | Aug. 14, 2016 (respiratory) | Sep. 13, 2016 (respiratory) | Sep. 6, 2016 (gastrointestinal) | Aug. 17, 2016 (respiratory) |
| Presence of fever (tactile* or measured) | Yes | No | Yes | Yes | No |
| Limbs affected (region) | 1 (left upper extremity) | 4 | 3 (bilateral upper extremities, right upper extremity) | 4 | 1 (left upper extremity) |
| No. of days illness to limb weakness onset | 2 | 6 | 2 | 2 | 10 |
| Cranial nerve features and timing | None | Facial droop subsequent to onset of limb weakness | Facial droop subsequent to onset of limb weakness | Facial droop before onset of limb weakness | Diplopia concurrent with limb weakness |
| Patient and family history of asthma | Asthma; Family history of asthma | Asthma | None | Family history of asthma | Mild asthma, seasonal allergies, food allergies, eczema |
| Corticosteroid history | Maintenance inhaled fluticasone; oral budesonide for asthma exacerbation Aug. 15-19, 2016 | Maintenance inhaled fluticasone; oral prednisolone for asthma exacerbation beginning Aug. 17, 2016 | None | Oral prednisolone for treatment of Bell's palsy beginning Sep. 5, 2016 | Maintenance inhaled fluticasone |
| Magnetic resonance imaging findings | T2** signal abnormalities in anterior and posterior columns of central grey cervical cord | T2** signal abnormality with anterior & posterior involvement, contiguous through multiple levels of cord | T2** signal abnormality in the anterior horn of the central grey cord | Anterior horn signal abnormality extending four cervical levels | Normal MRI |
| Cerebrospinal fluid white blood cells per mm$^3$ | 50 | 150 | 207 | 115 | 7 |
| Nasopharyngeal swab PCR results using Assay | Positive for EV-D68 | Positive for EV-D68 | Positive for EV-D68 | Unavailable | Unavailable |
| Stool specimen testing results | Negative enterovirus/ parechovirus by RT-PCR | Negative viral culture and enterovirus/ parechovirus by RT-PCR | Negative viral culture and enterovirus/ parechovirus by RT-PCR | Positive for coxsackievirus A10 by Sanger sequencing of the VP1 region | Unavailable |
| CSF Specimen — No. of days limb weakness to collection | 2 | 1 | 1 | 6 | 19 |
| CSF Specimen — EV-D68 Taqman Ct | Neg | Neg | Neg | Neg | Neg |
| CSF Specimen — EV-D68 amplicon read count | 0 | 0 | 0 | 0 | 0 |
| NP swab Specimen — No. of days limb weakness to collection | 4 | 1 | 7 | — | — |
| NP swab Specimen — EV-D68 Taqman Ct | 32.1 | 29.8 | 26.2 | — | — |
| NP swab Specimen — EV-D68 amplicon read count | 8 | 16 | 242 | — | — |

TABLE 3

Results for Patients 6-11

|  | Patient 6 | Patient 7 | Patient 8 | Patient 9 | Patient 10 | Patient 11 |
|---|---|---|---|---|---|---|
| AFM Case status | Unknown | ADEM | NMO | GBS | MS/ADEM | Unknown |
| Age at onset, gender | 12 yrs, female | 7.5 yrs, female | 17 yrs, male | 6.5 yrs, female | 14 yrs, female | 1.5 yrs, female |
| Onset date of focal limb weakness | Aug. 6, 2016 | Sep. 14, 2016 | Aug. 29, 2016 | Aug. 15, 2016 | Sep. 14, 2016 | Sep. 8, 2016 |
| Onset date of preceding respiratory or gastrointestinal illness | None | Sep. 14, 2016 (respiratory) | Aug. 19, 2016 (respiratory) | None | Sep. 8, 2016 (gastrointestinal) | None |
| Presence of fever (tactile* or measured) | No | Yes | No | Yes | No | Yes |
| No. Days illness to limb weakness onset | — | 0 | 10 | −31 | 6 | −14 |

TABLE 3-continued

Results for Patients 6-11

| | | Patient 6 | Patient 7 | Patient 8 | Patient 9 | Patient 10 | Patient 11 |
|---|---|---|---|---|---|---|---|
| Magnetic resonance imaging findings | | T3-7, 11-12 gray | C4, C6, T11 gray.white | C3-C7; T1, T10-11 gray/white | Normal | C1-5, 7; T1, 4-6, 11-12 | T4-T7 gray/white |
| Cerebrospinal fluid white blood cells per mm$^3$ | | 5 | 7 | 22 | 1 | 5 | 0 |
| CSF Specimen | No. of days limb weakness to specimen collection | 5 | 7 | 5 | 32 | 9 | 15 |
| | EV-D68 Taqman Ct | Neg | Neg | Neg | Neg | Neg | Neg |
| | EV-D68 amplicon read count | 0 | 0 | 0 | 0 | 0 | 0 |
| NP swab Specimen | No. of days limb weakness to specimen collection | — | 8 | — | — | 8 | 14 |
| | EV-D68 Taqman Ct | — | Neg | — | — | 31.0 | Neg |
| | EV-D68 amplicon read count | — | 0 | — | — | 36 | 0 |

Real-Time PCR and Targeted Amplicon Sequencing Results

Results of the real-time PCR are shown in TABLES 2 and 3 for each of the NP swab samples and CSF swab samples (see rows labeled "EV-D68 Taqman Ct"). Results of the amplicon sequencing method are shown in TABLES 2 and 3 for each of the NP swab samples and CSF swab samples (see rows labeled "EV-D68 amplicon read count").

Six of the 11 patients had nasopharyngeal (NP) swabs available for genomic analysis, including Patients 1, 2, 3, 7, 10, and 11. Genetic material from NP swabs (in the present example, the genetic material included RNA extracted from the NP swabs) from four of the six NP swab samples tested positive for EV-D68 by both real-time PCR and amplicon sequencing (see TABLE 2). The four NP swabs that were positive for EV-D68 using the assay were from Patients 1, 2, 3, and 10. Three of these EV-D68 positive results were from patients (Patients 1, 2, and 3) classified as confirmed cases of AFM, and one was from a patient (Patient 10) with differential diagnoses of acute disseminated encephalomyelitis (ADEM) or multiple sclerosis (MS). NP swabs from Patient 4, a confirmed AFM case, and from Patient 5, the single probable AFM case, were not available for genomic analysis. CSF was collected from all eleven patients. None of the CSF specimens tested positive for EV-D68.

Polymorphisms were identified among the amplicon sequences of each sample. Not including the primer regions, the VP1 gene sequence of the NP swab sample from Patient 1 was one SNP different from a 2015 Japan isolate (Genbank accession LC203572) and several 2013-2014 Philippines isolates (AB992437, AB992417, KX789257, KX789240). The NP swab sample from Patient 2 was one SNP different from the five above (at a different locus) and from a 2016 Denmark isolate (KY457569). Additionally, NP swab samples from Patient 10 and Patient 3 were a perfect match to many global strains from 2013 to 2017.

In summary, real-time PCR and amplicon sequencing detected EV-D68 virus RNA in the three AFM patients from which NP swabs were collected, as well as in a fourth patient diagnosed with ADEM, a disease that commonly follows bacterial or viral infections, including enterovirus. No other etiological causes for AFM were found by 16S or RNA/DNA metagenomic sequencing in these cases, strengthening the likelihood that EV-D68 is a cause.

16S Microbiomic Analysis

The whole metagenome sequencing comprised microbiome analysis by metagenomic sequencing of RNA and 16S rRNA gene sequencing of DNA extracted from CSF. The mean number of 16S sequence reads generated in the nine CSF samples analyzed for bacterial population was 1,612, with five samples having less than (<) 200 reads. Of the six NP swabs analyzed for bacterial population, two samples generated less than (<) 4000 reads, while the other four averaged 37,128 reads. The 16S PCR reagent blank (negative control) yielded 91 reads.

The bacterial composition (considering all taxa at >1% of the total, after the reagent blank taxa were removed) of all NP swabs was characterized by normal upper respiratory flora such as *Corynebacterium, Bacillus, Propiniobacterium, Streptococcus, Fusobacterium, Prevotella, Atopobium, Rothia, Veillonella, Leptotrichia* and *Haemophilus*. The sample size was too small to detect differences in NP bacterial communities. Five of the six NP swabs contained a small number of unknown taxa. The variation in composition between patients appeared analogous to the variation seen among healthy subjects. Four of the six NP swabs were collected from patients with recent respiratory illness (Patients 1, 2, 3, and 7). However, the swabs were collected between six and nine days after the onset of the respiratory illness (after focal limb weakness became apparent). The other two patients (Patients 10 and 11) had gastrointestinal illness or fever, respectively.

As shown in FIG. 1, the unpaired reads from Patient 1 cover 132 bases of the p3D gene and overlap for 48 bases. The sequence was a perfect match to several 2016 genomes from an outbreak in the Lower Hudson Valley, N.Y. in 2016, including NY230_16 (KY385890, at positions 6862-6993), NY172_16, NY141_16, and NY135_16, and other genomes including NY75_16, and USA/TX/2016-19506 and USA/FL/2016-19504. These latter two genomes were isolated from confirmed AFM cases. For the paired reads from Patient 3, the forward read aligns to the p2A protease gene for 35 bases and the p2B polypeptide gene for 58 bases (KY385890 positions 3665-3757 with two SNPs). The best BLAST hit is to three 2015 genomes from Osaka City, Japan (LC107898, LC107899, LC107901), with one SNP. The reverse read aligns to the p2B polypeptide gene (KY385890 positions 3799-3891 with one SNP). Best BLAST hits include many genomes, all with one SNP. Additionally, NP swab samples from Patient 10 and Patient 3 were a perfect match to many global strains from 2013 to 2017.

There was no evidence of CSF bacterial infection in any patients, as 16S read counts were low and no specimens were dominated by one organism, except a sample from Patient 11, characterized by Corynebacterium, a known CSF culture contaminant and laboratory contaminant. The low 16S read counts possibly highlighted several bacterial contaminants potentially introduced during sample processing and preparation for sequencing, as documented previously. Bacterial taxa found in the CSF specimens included *Propionibacterium, Bacillus* and Enterobacteriaceae, all known to be CSF culture contaminants and laboratory contaminants; and *Chryseobacterium, Delftia, Methylobacterium, Ralstonia, Roseomonas*, Caulobacteriaceae, and Bradyrhizobiaceae, all known laboratory contaminants, but also recently shown to be part of the skin microbiome as are *Staphylococcus, Prevotella*, and *Sediminibacterium*, which could be specimen collection contaminants. Some organisms were present in both the NP bacterial population and in the CSF data of a patient, such as *Moryella, Fusobacterium*, and *Oribacterium* in Patient 10, suggesting the possibility of crossover of these organisms to the patient's skin and contamination of the CSF specimen. *Parvimonas*, part of the normal oral flora, was found in one CSF sample (without a NP swab from the same patient to compare), suggesting a possible transfer from the skin. Other organisms, generally not associated with clinical disease, were found in some CSF samples at relatively high proportion (*Actinoplanes, Tepidimicrobium*, Rhodospirillaceae, and *Kaistobacter*), but total read counts were very low for those samples (<200 reads), thus their low-level presence potentially indicates contamination. Two CSF samples had reads from unknown taxa.

No common etiology for AFM or for respiratory illness was found from the bacterial population analyses of the CSF and NP swab specimen DNA.

DNA and RNA Metagenomics Analysis

In both the CSF and NP swab metagenomic data samples, human sequence data were most common. Microorganism metagenomic results largely agreed with the 16S microbiomic analyses in organisms identified for the NP swabs, and in identification of probable contamination in the CSF samples. From the metagenomic analyses, like the microbiomic analysis, no other bacterial etiology was found for the neurological illnesses in this outbreak.

Herpes simplex virus (HSV), a known neuroinvasive pathogen, was the top viral DNA hit (from the MTS analysis) in two of the CSF metagenomic samples, Patient 8 and Patient 4 (TABLE 4). A sample from Patient 8 was from a patient diagnosed with neuromyelitis optica, and a sample from Patient 4 was from an AFM case, where the patient was also noted to have a cold sore at the time of examination. Neither of these patients had NP swabs available for testing.

TABLES 4-6 show metagenomic and total RNA results from three analysis tools: MetaSeq, GOTTCHA, and MetaPhlAn. For MetaSeq analysis in TABLE 4, the top five hits at >0.1% of the total signature hits after removal of human reads are listed. For GOTTCHA analysis in TABLE 5, the top five hits of the bacterial and viral databases with greater than (>) 100 reads are listed. For MetaPhlAn analysis in TABLE 6, the top five or all hits of the marker library at greater than 1.0% of all hits are listed, except for taxa in parentheses, which are the top hits below the abundance threshold. Each row in TABLES 4-6 includes the samples from a single patient.

TABLE 4

| Metagenomic and total RNA results from MetaSeq | | | |
|---|---|---|---|
| CSF samples | | NP swab samples | |
| Patient No. | Top 5 hits at >0.1% of data minus human | Patient No. | Top 5 hits at >0.1% of database minus human |
| 6 | *Micrococcus luteus, Acinetobacter guillouiae, Propionibacterium acnes, Staphylococcus epidermidis, Acinetobacter baumannii* | — | — |
| 8 | *Micrococcus luteus* | — | — |
| 8 (DNA) | (Human herpesvirus 1) | — | — |
| 4 | *Micrococcus luteus* | — | — |
| 4 (DNA) | (Human herpesvirus 1) | — | — |
| 5 | *Micrococcus luteus, Acinetobacter guillouiae* | — | — |
| 9 | *Micrococcus luteus, Acinetobacter guillouiae, Staphylococcus epidermidis, Propionibacterium acnes* | — | — |
| 7 | *Micrococcus luteus, Propionibacterium acnes* | 7 | *Veillonella parvula, Haemophilus parainfluenzae, Fusobacterium nucleatum, Capnocytophaga ochracea* |
| 1 | *Micrococcus luteus, Propionibacterium acnes, Acinetobacter guillouiae* | 1 | No hits |
| — | — | 1 (DNA) | (Human herpesvirus 1) |
| 2 | *Micrococcus luteus, Alphapapillomavirus 9, Enterobacteria phage phiX174 sensu lato, Propionibacterium acnes, Waddlia chondrophila* | 2 | *Staphylococcus epidermidis, Bacillus coagulans, Thermoanaerobacterium thermosaccharolyticum, Haemophilus influenzae, Alicyclobacillus acidocaldarius* |

TABLE 4-continued

Metagenomic and total RNA results from MetaSeq

| CSF samples | | NP swab samples | |
|---|---|---|---|
| Patient No. | Top 5 hits at >0.1% of data minus human | Patient No. | Top 5 hits at >0.1% of database minus human |
| 10 | *Micrococcus luteus* | 10 | *Prevotella melaninogenica, Fusobacterium nucleatum, Veillonella parvula, Streptococcus parasanguinis, Streptococcus mitis* |
| 3 | *Micrococcus luteus, Propionibacterium acnes, Acinetobacter guillouiae* | 3 | *Veillonella parvula, Streptococcus parasanguinis, Streptococcus salivarius, Atopobium parvulum, Prevotella melaninogenica* |
| — | — | 3 (DNA) | (*Streptococcus salivarius*) |
| 11 | *Micrococcus luteus, Propionibacterium acnes, Acinetobacter guillouiae, Staphylococcus epidermidis* | 11 | *Veillonella parvula, Streptococcus salivarius, Streptococcus mitis, Streptococcus parasanguinis, Streptococcus pneumoniae* |
| — | — | 11 (DNA) | (*Streptococcus salivarius*) |

As shown in TABLE 4, MTS analyses identified *Micrococcus luteus* as the top non-human hit in all CSF RNA samples and *Acinetobacter guillouiae* was consistently identified among the top five signature hits, both common laboratory contaminants. These species were absent or at very low levels in the 16S analysis, and not in any of the DNA metagenomic analyses, indicating likely contamination during the total RNA sample preparation. Other signature hits include *Propionibacterium acnes* and *Staphylococcus epidermidis*, also noted in the 16S microbiomic analysis. Nearly all top signature hits found in the NP swab metagenomic data matched those found in the 16S data. One sample from Patient 1, yielded no signature hits. HSV RNA was not identified in any RNA sample.

In TABLE 5, GOTTCHA analysis largely agreed with the MTS results for the NP swabs, although in some cases (Patient 7 and Patient 2) MTS identified more species, and in other cases (Patient 3 and Patient 11) GOTTCHA identified an organism in the DNA that MTS detected only in the RNA (TABLE 5). GOTTCHA additionally identified in all CSF RNA samples and several NP swabs human endogenous retrovirus K (HERV-K), which has been implicated in neurodegeneration, and its expression has been associated with amyotrophic lateral sclerosis (ALS), MS, rheumatoid arthritis (RA), schizophrenia, HIV-associated dementia, and cancer. One CSF RNA sample was positive for HSV at a low level (Patient 2, from an AFM case whose NP swab was positive for EV-D68).

TABLE 5

Metagenomic and total RNA results from GOTTCHA

| CSF samples | | NP swab samples | |
|---|---|---|---|
| Patient No. | All hits with >100 reads from bacterial and viral databases | Patient No. | Top 5 hits in abundance with >100 reads from bacterial and viral databases |
| 6 | HERV-K | — | — |
| 8 | HERV-K | — | — |
| 8 (DNA) | HERV-K | — | — |
| 4 | HERV-K | — | — |
| 4 (DNA) | (*Streptococcus pneumoniae*) | — | — |
| 5 | HERV-K, Enterobacteria phage | — | — |
| 9 | HERV-K | — | — |
| 7 | HERV-K | 7 | HERV-K, *Haemophilus parainfluenzae*, Enterobacteria phage |
| 1 | HERV-K | 1 | HERV-K, Enterobacteria phage, Human herpesvirus 6A |
| — | — | 1 (DNA) | HERV-K |
| 2 | HERV-K, Enterobacteria phage, Human herpesvirus 6A | 2 | HERV-K, *Staphylococcus epidermidis* |
| 10 | HERV-K | 10 | *Prevotella melaninogenica, Fusobacterium nucleatum, Veillonella parvula, Streptococcus mitis, Streptococcus parasanguinis* |
| 3 | HERV-K | 3 | *Veillonella parvula*, HERV-K, *Streptococcus parasanguinis, Streptococcus salivarius, Streptococcus mitis* |
| — | — | 3 (DNA) | HERV-K, *Streptococcus parasanguinis, Streptococcus salivarius, Veillonella parvula, Rothia mucilaginosa,* |

TABLE 5-continued

Metagenomic and total RNA results from GOTTCHA

| CSF samples | | NP swab samples | |
|---|---|---|---|
| Patient No. | All hits with >100 reads from bacterial and viral databases | Patient No. | Top 5 hits in abundance with >100 reads from bacterial and viral databases |
| 11 | HERV-K | 11 | HERV-K, *Veillonella parvula*, *Streptococcus salivarius*, *Streptococcus parasanguinis*, *Streptococcus mitis* |
| — | — | 11 (DNA) | HERV-K, *Streptococcus salivarius*, *Veillonella parvula*, *Streptococcus parasanguinis*, *Rothia mucilaginosa* |

MetaPhlAn results in TABLE 6 included several additional bacterial identifications in the NP swabs not found with MTS or GOTTCHA, though many species were of the same genera. MetaPhlAn, like GOTTCHA, identified HERV-K in all CSF samples and several NP swabs. MetaPhlAn did not identify HSV in any CSF sample.

NP swab sample from Patient 1, one forward and one reverse read (unpaired) aligned to the p3D RNA polymerase region. In the NP swab sample from Patient 3, a paired forward and reverse read specifically matched EV-D68, aligning to p2A and p2B genes.

TABLE 6

Metagenomic and total RNA results from MetaPhlAn

| CSF samples | | NP swab samples | |
|---|---|---|---|
| Patient No. | All Hits >1.0% | Patient No. | Top 5 Hits >1.0% |
| 6 | HERV-K | — | — |
| 8 | HERV-K | — | — |
| 8 (DNA) | Enterobacteria phage, HERV-K, *Granulicatella*, *Streptococcus mitis* | — | — |
| 4 | HERV-K | — | — |
| 4 (DNA) | Enterobacteria phage, HERV-K, *Granulicatella*, *Streptococcus mitis* | — | — |
| 5 | HERV-K | — | — |
| 9 | HERV-K | — | — |
| 7 | HERV-K | 7 | Enterobacteria phage, Abelson murine leukemia virus, *Veillonella*, *Capnocytophaga* |
| 1 | Enterobacteria phage, HERV-K | 1 | HERV-K |
| — | — | 1 (DNA) | Enterobacteria phage, HERV-K |
| 2 | HERV-K, woolly monkey sarcoma virus | 2 | Enterobacteria phage, HERV-K, *Enterococcus cecorum*, *Alicyclobacillus* |
| 10 | HERV-K | 10 | *Veillonella*, *Prevotella pallens*, *Prevotella histicola*, *Prevotella* sp., *Veillonella atypica* |
| 3 | HERV-K | 3 | *Veillonella*, HERV-K, *Streptococcus parasanguinis*, *Streptococcus salivarius*, *Veillonella atypica* |
| — | — | 3 (DNA) | Enterobacteria phage, HERV-K, *Streptococcus salivarius*, *Streptococcus parasanguinis*, *Veillonella* |
| 11 | Enterobacteria phage, HERV-K | 11 | *Streptococcus* sp., *Dolosigranulum pigrum*, HERV-K, *Veillonella atypical*, *Streptococcus mitis* |
| — | — | 11 (DNA) | *Streptococcus* sp, *Dolosigranulum pigrum*, HERV-K, *Veillonella atypica*, *Veillonella* sp. |

Targeted Query of Metagenomic Data

In addition to the metagenomic analysis pipelines, a specific query was performed for any reads matching EV-D68 or HERV-K in the metagenomic data with ASAP (utilizing bowtie2 with no read clipping). EV-D68 specific reads were found in two samples that were EV-D68 positive by real-time PCR and amplicon sequencing (FIG. 1). In the In the present case cluster, the EV-D68 real-time PCR required a pre-amplification step, and metagenomic analysis resulted in limited presence of EV-D68 reads, suggesting that the viral RNA was at very low levels, possibly due to actual low viral loads or RNA degradation. The disclosed PCR and sequencing results found that NP swabs from all three confirmed AFM patients for which swabs were available were positive for EV-D68, adding to the strength and consistency of evidence supporting an EV-D68 etiology of AFM. No NP swabs were available from the fourth confirmed case or single "probable" case. A case of ADEM included in the cluster investigation also had an EV-D68 positive NP swab. The non-AFM EV-D68-positive sample was a NP swab from a Patient 10 whose differential diagnoses included ADEM or MS at the time of sample collection. Enteroviruses are a known cause of ADEM, including viral type D68 specifically. Additionally, ADEM and MS have overlapping diagnostic criteria with AFM. Among the many diagnostic criteria, ADEM is characterized by lesions in the white and gray matter evident from magnetic resonance imaging (MRI), and the lesion patterns are variable. The remaining five suspect cases (Patents 6-11) in the cluster were negative for EV-D68 by all genomic analyses.

Identification of the etiology of AFM and related illnesses is important in order to understand risk factors, target surveillance, properly treat diagnosed AFM patients, and to help limit future outbreaks. Emphasis must be placed on the timely collection and appropriate handling of patient specimens in order to increase the likelihood of detection of RNA viruses, in this case EV-D68 detection. Acknowledgement of EV-D68 as a likely etiologic agent of AFM could allow for improved surveillance and response, and provide support for resource expenditure for vaccine development to eventually prevent AFM or other EV-D68 neurologic disease.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES

The publications discussed herein are provided solely for their disclosure prior to the filing date of the present application. Nothing herein is to be construed as an admission that the present invention is not entitled to antedate such publication by virtue of prior invention.

1. CDC. Notes from the field: acute flaccid myelitis among persons aged ≤21 years—United States, Aug. 1-Nov. 13, 2014. MMWR Morb Mortal Wkly Rep. 2015; 63:1243-4.

2. Pastula D M, et al. Acute neurologic illness of unknown etiology in children—Colorado, August-September 2014. Morb Mortal Wkly Rep. 2014; 10; 63:901-2

3. Sejvar J J, et al. Acute flaccid myelitis in the United States, August-December 2014: results of nationwide surveillance. Clin Infect Dis 2016; 63:737-45.

4. Council of State and Territorial Epidemiologists (CSTE). CSTE position statement, 15-ID-01: Standardized case definition for acute flaccid myelitis.

5. Colman R E, et al. Rapid drug susceptibility testing of drug-resistant *Mycobacterium tuberculosis* isolates directly from clinical samples by use of amplicon sequencing: a proof-of-concept study. J Clin Microbiol 2016; 54(8):2058-67.

6. Bowers J R, et al. KlebSeq, a diagnostic tool for surveillance, detection, and monitoring of *Klebsiella pneumoniae*. J Clin Microbiol 2016; 54(10):2582-96.

7. Grice E A, Segre J A. The skin microbiome. Nat Rev Microbiol 2011; 9:244-53.

8. Noor A, Krilov L R. 2016. Enterovirus Infections. Pediatr Rev 37:505-515.

9. Nathanson N, Kew O M. 2010. From emergence to eradication: the epidemiology of poliomyelitis deconstructed. Am J Epidemiol 172:1213-1229.

10. Suresh S, Forgie S, Robinson J. 2018. Non-polio Enterovirus detection with acute flaccid paralysis: A systematic review. J Med Virol 90:3-7.

11. Wiznitzer M, Nath A. 2017. Acute flaccid myelitis and enterovirus D68: Deja vu all over again. Neurology 89:112-113.

12. Tokarz R, et al. 2012. Worldwide emergence of multiple clades of enterovirus 68. J Gen Virol 93:1952-1958.

13. Maloney J A, et al. 2015. MRI findings in children with acute flaccid paralysis and cranial nerve dysfunction occurring during the 2014 enterovirus D68 outbreak. AJNR Am J Neuroradiol 36:245-250.

14. Greninger A L, et al. 2015. A novel outbreak enterovirus D68 strain associated with acute flaccid myelitis cases in the USA (2012-14): a retrospective cohort study. Lancet Infect Dis 15:671-682.

15. Messacar K, et al. 2015. A cluster of acute flaccid paralysis and cranial nerve dysfunction temporally associated with an outbreak of enterovirus D68 in children in Colorado, USA. Lancet 385:1662-1671.

16. Aliabadi N, et al. 2016. Enterovirus D68 Infection in Children with Acute Flaccid Myelitis, Colorado, USA, 2014. Emerg Infect Dis 22:1387-1394.

17. Ayscue P, et al. 2014. Acute flaccid paralysis with anterior myelitis—California, June 2012-June 2014. MMWR Morb Mortal Wkly Rep 63:903-906.

18. Van Haren K, et al. 2015. Acute Flaccid Myelitis of Unknown Etiology in California, 2012-2015. JAMA 314: 2663-2671.

19. Lang M, et al. 2014. Acute flaccid paralysis following enterovirus D68 associated pneumonia, France, 2014. Euro Surveill 19.

20. Cabrerizo M, et al. 2017. First Cases of Severe Flaccid Paralysis Associated with Enterovirus D68 Infection in Spain, 2015-2016. Pediatr Infect Dis J doi:10.1097/INF.0000000000001668.

21. Dyrdak R, et al. 2016. Outbreak of enterovirus D68 of the new B3 lineage in Stockholm, Sweden, August to September 2016. Euro Surveill 21.

22. Chong P F, et al. 2017. Clinical Features of Acute Flaccid Myelitis Temporally Associated with an Enterovirus D68 Outbreak: Results of a Nationwide Survey of Acute Flaccid Paralysis in Japan, August-December 2015. Clin Infect Dis doi:10.1093/cid/cix860.

23. Wang G, et al. 2017. Enterovirus D68 Subclade B3 Strain Circulating and Causing an Outbreak in the United States in 2016. Sci Rep 7:1242.

24. Knoester M, et al. 2017. Upsurge of Enterovirus D68, the Netherlands, 2016. Emerg Infect Dis 23:140-143.

25. Del Gaudio S, et al. 2013. Preamplification procedure for the analysis of ancient DNA samples. ScientificWorldJournal 2013:734676.

26. Del Gaudio S, et al. 2010. A preamplification approach to GMO detection in processed foods. Anal Bioanal Chem 396:2135-2142.

27. Lal D, Keim P, Delisle J. 2017. Mapping and Comparing Bacterial Microbiota in the Sinonasal Cavity of Healthy, Allergic Rhinitis, and Chronic Rhinosinusitis Subjects. International Forum of Allergy and Rhinology.

28. Klindworth A, et al. 2013. Evaluation of general 16S ribosomal RNA gene PCR primers for classical and next-generation sequencing-based diversity studies. Nucleic Acids Res 41:e1.

29. Caporaso J G, et al. 2010. QIIME allows analysis of high-throughput community sequencing data. Nat Methods 7:335-336.

30. Edgar R C. 2010. Search and clustering orders of magnitude faster than BLAST. Bioinformatics 26:2460-2461.

31. Caporaso J G, et al. 2010. PyNAST: a flexible tool for aligning sequences to a template alignment. Bioinformatics 26:266-267.

32. DeSantis T Z, et al. 2006. Greengenes, a chimera-checked 16S rRNA gene database and workbench compatible with ARB. Appl Environ Microbiol 72:5069-5072.

33. Haas B J, et al. 2011. Chimeric 16S rRNA sequence formation and detection in Sanger and 454-pyrosequenced PCR amplicons. Genome Res 21:494-504.

34. McDonald D, et al. 2012. An improved Greengenes taxonomy with explicit ranks for ecological and evolutionary analyses of bacteria and archaea. ISME J 6:610-618.

35. Freitas T A, et al. 2015. Accurate read-based metagenome characterization using a hierarchical suite of unique signatures. Nucleic Acids Res 43:e69.

36. Segata N, et al. 2012. Metagenomic microbial community profiling using unique clade-specific marker genes. Nat Methods 9:811-814.

37. Perry A, Schneider T, Fofanov V. 2017. MetaSeQ: Fast Metagenomic Binning Poster presentation. Jun. 21, 2017, Las Vegas, Nev.

38. Ackelsberg J, Rakeman J, Hughes S, Petersen J, Mead P, Schriefer M, Kingry L, Hoffmaster A, Gee J E. 2015. Lack of Evidence for Plague or Anthrax on the New York City Subway. Cell Syst 1:4-5.

39. Afshinnekoo E, et al. 2015. Modern Methods for Delineating Metagenomic Complexity. Cell Syst 1:6-7.

40. Afshinnekoo E, et al. 2015. Geospatial Resolution of Human and Bacterial Diversity with City-Scale Metagenomics. Cell Syst 1:97-97 e93.

41. Merchant S, Wood D E, Salzberg S L. 2014. Unexpected cross-species contamination in genome sequencing projects. PeerJ 2:e675.

42. Schmieder R, Edwards R. 2011. Fast identification and removal of sequence contamination from genomic and metagenomic datasets. PLoS One 6:e17288.

43. Tao Z Y, Sui X, Jun C, Culleton R, Fang Q, Xia H, Gao Q. 2015. Vector sequence contamination of the Plasmodium vivax sequence database in PlasmoDB and In silico correction of 26 parasite sequences. Parasit Vectors 8:318.

44. Li H, Durbin R. 2009. Fast and accurate short read alignment with Burrows-Wheeler transform. Bioinformatics 25:1754-1760.

45. Langmead B, Salzberg S L. 2012. Fast gapped-read alignment with Bowtie 2. Nat Methods 9:357-359.

46. Ondov B D, Treangen T J, Melsted P, Mallonee A B, Bergman N H, Koren S, Phillippy A M. 2016. Mash: fast genome and metagenome distance estimation using MinHash. Genome Biol 17:132.

47. Bowers J R, et al. 2018. Direct detection of Coccidioides from Arizona soils using CocciENV, a highly sensitive and specific real-time PCR assay. Med Mycol doi: 10.1093/mmy/myy007.

48. Bolger A M, Lohse M, Usadel B. 2014. Trimmomatic: a flexible trimmer for Illumina sequence data. Bioinformatics 30:2114-2120.

49. Milne I, Stephen G, Bayer M, Cock P J, Pritchard L, Cardle L, Shaw P D, Marshall D. 2013. Using Tablet for visual exploration of second-generation sequencing data. Brief Bioinform 14:193-202.

50.

51. Biswas K, Hoggard M, Jain R, Taylor M W, Douglas R G. 2015. The nasal microbiota in health and disease: variation within and between subjects. Front Microbiol 9:134.

52. Bassis C M, Tang A L, Young V B, Pynnonen M A. 2014. The nasal cavity microbiota of healthy adults. Microbiome 2:27.

53. Wong P H, Maranich A M, Muench D F. 2013. Isolation of bacterial cerebrospinal fluid culture contaminants at a major military medical center. Diagn Microbiol Infect Dis 77:357-361.

54. Salter S J, Cox M J, Turek E M, Calus S T, Cookson W O, Moffatt M F, Turner P, Parkhill J, Loman N J, Walker A W. 2014. Reagent and laboratory contamination can critically impact sequence-based microbiome analyses. BMC Biol 12:87.

55. Boysen M M, Henderson J L, Rudkin S E, Burns M J, Langdorf M I. 2009. Positive cerebrospinal fluid cultures after normal cell counts are contaminants. J Emerg Med 37:251-256.

56. Olson D A, Hoeprich P D. 1984. Analysis of bacterial isolates from cerebrospinal fluid. J Clin Microbiol 19:144-146.

57. Cosseau C, Romano-Bertrand S, Duplan H, Lucas O, Ingrassia I, Pigasse C, Rogues C, Jumas-Bilak E. 2016. Proteobacteria from the human skin microbiota: Species-level diversity and hypotheses. One Health 2:33-41.

58. Gao Z, Tseng C H, Pei Z, Blaser M J. 2007. Molecular analysis of human forearm superficial skin bacterial biota. Proc Natl Acad Sci USA 104:2927-2932.

59. Li W, Lee M H, Henderson L, Tyagi R, Bachani M, Steiner J, Campanac E, Hoffman D A, von Geldern G, Johnson K, Maric D, Morris H D, Lentz M, Pak K, Mammen A, Ostrow L, Rothstein J, Nath A. 2015. Human endogenous retrovirus-K contributes to motor neuron disease. Sci Transl Med 7:307ra153.

60. Bowen L N, Tyagi R, Li W, Alfahad T, Smith B, Wright M, Singer E J, Nath A. 2016. HIV-associated motor neuron disease: HERV-K activation and response to antiretroviral therapy. Neurology 87:1756-1762.

61. Morandi E, Tanasescu R, Tarlinton R E, Constantinescu C S, Zhang W, Tench C, Gran B. 2017. The association between human endogenous retroviruses and multiple sclerosis: A systematic review and meta-analysis. PLoS One 12:e0172415.

62. Hohn O, Hanke K, Bannert N. 2013. HERV-K(HML-2), the Best Preserved Family of HERVs: Endogenization, Expression, and Implications in Health and Disease. Front Oncol 3:246.

63. Christensen T. 2016. Human endogenous retroviruses in neurologic disease. APMIS 124:116-126.

64. Ruggieri V, Paz M I, Peretti M G, Rugilo C, Bologna R, Freire C, Vergel S, Savransky A. 2017. Enterovirus D68 infection in a cluster of children with acute flaccid myelitis, Buenos Aires, Argentina, 2016. Eur J Paediatr Neurol 21:884-890.

65. Engelmann I, Fatoux M, Lazrek M, Alidjinou E K, Mirand A, Henquell C, Dewilde A, Hober D. 2017. Enterovirus D68 detection in respiratory specimens: Association with severe disease. J Med Virol 89:1201-1207.

66. Hixon A M, Yu G, Leser J S, Yagi S, Clarke P, Chiu C Y, Tyler K L. 2017. A mouse model of paralytic myelitis caused by enterovirus D68. PLoS Pathog 13:e1006199.

67. Dyda A, Stelzer-Braid S, Adam D, Chughtai A A, MacIntyre C R. 2018. The association between acute flaccid myelitis (AFM) and Enterovirus D68 (EV-D68)—what is the evidence for causation? Eurosurveillance 23:17-00310.

68. Guerra J A, Waters A, Kelly A, Morley U, O'Reilly P, O'Kelly E, Dean J, Cunney R, O'Lorcain P, Cotter S, Connell J, O'Gorman J, Hall W W, Carr M, De Gascun C F. 2017. Seroepidemiological and phylogenetic characterization of neurotropic enteroviruses in Ireland, 2005-2014. J Med Virol 89:1550-1558.

69. Bonwitt J, Poel A, DeBolt C, Gonzales E, Lopez A, Routh J, Rietberg K, Linton N, Reggin J, Sejvar J, Lindquist S, Otten C. 2017. Acute Flaccid Myelitis Among Children—Washington, September-November 2016. MMWR Morb Mortal Wkly Rep 66:826-829.

70. Kreuter J D, Barnes A, McCarthy J E, Schwartzman J D, Oberste M S, Rhodes C H, Modlin J F, Wright P F. 2011. A fatal central nervous system enterovirus 68 infection. Arch Pathol Lab Med 135:793-796.

71. Khetsuriani N, Lamonte-Fowlkes A, Oberst S, Pallansch M A, Centers for Disease C, Prevention. 2006. Enterovirus surveillance—United States, 1970-2005. MMWR Surveill Summ 55:1-20.

72. Giombini E, Rueca M, Barberi W, Iori A P, Castilletti C, Scognamiglio P, Vairo F, Ippolito G, Capobianchi M R, Valli M B. 2017. Enterovirus D68-Associated Acute Flaccid Myelitis in Immunocompromised Woman, Italy. Emerg Infect Dis 23:1690-1693.

73. Anonymous. 2016. Rapid Risk Assessment—Enterovirus detections associated with severe neurological symptoms in children and adults in European countries. European Center for Disease Prevention and Control, ECDC, Stockholm.

74. Liu D. 2016. Molecular Detection of Human Viral Pathogens. CRC Press.

75. Varghese R, Iyer A, Hunter K, Cargill J S, Cooke R P. 2015. Sampling the upper respiratory tract for enteroviral infection is important in the investigation of an acute neurological illness in children. Eur J Paediatr Neurol 19:494-495.

76. Bale J F, Jr. 2015. Virus and Immune-Mediated Encephalitides: Epidemiology, Diagnosis, Treatment, and Prevention. Pediatr Neurol 53:3-12.

77. Hixon A M, Clarke P, Tyler K L. 2017. Evaluating treatment efficacy in a mouse model of enterovirus D68 paralytic myelitis. J Infect Dis doi:10.1093/infdis/jix468.

78. Unger S A, Bogaert D. 2017. The respiratory microbiome and respiratory infections. J Infect 74 Suppl 1:S84-S88.

79. Huang W, Wang G, Zhuge J, Nolan S M, Dimitrova N, Fallon J T. 2015. Whole-Genome Sequence Analysis Reveals the Enterovirus D68 Isolates during the United States 2014 Outbreak Mainly Belong to a Novel Clade. Sci Rep 5:15223.

80. Gong Y N, Yang S L, Shih S R, Huang Y C, Chang P Y, Huang C G, Kao K C, Hu H C, Liu Y C, Tsao K C. 2016. Molecular evolution and the global reemergence of enterovirus D68 by genome-wide analysis. Medicine (Baltimore) 95:e4416.

81. Ng T F, Montmayeur A, Castro C, Cone M, Stringer J, Lamson D M, Rogers S L, Wang Chern S W, Magana L, Marine R, Rubino H, Serinaldi D, George K S, Nix W A. 2016. Detection and Genomic Characterization of Enterovirus D68 in Respiratory Samples Isolated in the United States in 2016. Genome Announc 4.

82. Kuss S K, Best G T, Etheredge C A, Pruijssers A J, Frierson J M, Hooper L V, Dermody T S, Pfeiffer J K. 2011. Intestinal microbiota promote enteric virus replication and systemic pathogenesis. Science 334:249-252.

83. de Steenhuijsen Piters W A, Heinonen S, Hasrat R, Bunsow E, Smith B, Suarez-Arrabal M C, Chaussabel D, Cohen D M, Sanders E A, Ramilo O, Bogaert D, Mejias A. 2016. Nasopharyngeal Microbiota, Host Transcriptome, and Disease Severity in Children with Respiratory Syncytial Virus Infection. Am J Respir Crit Care Med 194:1104-1115.

84. Gonzalez-Hernandez M J, Cavalcoli J D, Sartor M A, Contreras-Galindo R, Meng F, Dai M, Dube D, Saha A K, Gitlin S D, Omenn G S, Kaplan M H, Markovitz D M. 2014. Regulation of the human endogenous retrovirus K (HML-2) transcriptome by the HIV-1 Tat protein. J Virol 88:8924-8935.

85. Granerod J, Davies N W, Mukonoweshuro W, Mehta A, Das K, Lim M, Solomon T, Biswas S, Rosella L, Brown D W, Crowcroft N S, Group UKPHEAoES. 2016. Neuroimaging in encephalitis: analysis of imaging findings and interobserver agreement. Clin Radiol 71:1050-1058.

86. De Bolle L, Van Loon J, De Clercq E, Naesens L. 2005. Quantitative analysis of human herpesvirus 6 cell tropism. J Med Virol 75:76-85.

87. Saitoh A, Sawyer M H, Leake J A. 2004. Acute disseminated encephalomyelitis associated with enteroviral infection. Pediatr Infect Dis J 23:1174-1175.

88. Wali R K, Lee A H, Kam J C, Jonsson J, Thatcher A, Poretz D, Ambardar S, Piper J, Lynch C, Kulkarni S, Cochran J, Djurkovic S. 2015. Acute Neurological Illness in a Kidney Transplant Recipient Following Infection With Enterovirus-D68: An Emerging Infection? Am J Transplant 15:3224-3228.

89. Pillai S, Tantsis E, Prelog K, Ramanathan S, Webster R, Ouvrier R A, Kesson A, Brilot F, Dale R C. 2015. Confirmed enterovirus encephalitis with associated steroid-responsive acute disseminated encephalomyelitis: an overlapping infection and inflammation syndrome. Eur J Paediatr Neurol 19:266-270.

90. Britton P N, Khoury L, Booy R, Wood N, Jones C A. 2016. Encephalitis in Australian children: contemporary trends in hospitalisation. Arch Dis Child 101:51-56.

91. Kim J M, Son C N, Chang H W, Kim S H. 2015. Simultaneous presentation of acute disseminated encephalomyelitis (ADEM) and systemic lupus erythematosus (SLE) after enteroviral infection: can ADEM present as the first manifestation of SLE? Lupus 24:633-637.

92. Wender M. 2011. Acute disseminated encephalomyelitis (ADEM). J Neuroimmunol 231:92-99.

93. Martin J A, Messacar K, Yang M L, Maloney J A, Lindwall J, Carry T, Kenyon P, Sillau S H, Oleszek J, Tyler K L, Dominguez S R, Schreiner T L. 2017. Outcomes of Colorado children with acute flaccid myelitis at 1 year. Neurology 89:129-137.

94. Huang W, Yin C, Zhuge J, Farooq T, Yoon E C, Nolan S M, Chen D, Fallon J T, Wang G. 2016. Complete Genome Sequences of Nine Enterovirus D68 Strains from Patients of the Lower Hudson Valley, N.Y., 2016. Genome Announc 4.

95. Kaida A, Iritani N, Yamamoto S P, Kanbayashi D, Hirai Y, Togawa M, Amo K, Kohdera U, Nishigaki T, Shiomi M, Asai S, Kageyama T, Kubo H. 2017. Distinct genetic clades of enterovirus D68 detected in 2010, 2013, and 2015 in Osaka City, Japan. PLoS One 12:e0184335.

What is claimed is:

1. A method of detecting Enterovirus D68 in a subject, comprising:
producing an amplicon by amplifying a nucleic acid segment from a sample obtained from the subject with,
(a) a first primer comprising SEQ ID NO: 8,
(b) a second primer comprising SEQ ID NO: 9,
(c) a third primer comprising SEQ ID NO: 10,
(d) a fourth primer comprising SEQ ID NO: 11, and
(e) a fifth primer comprising SEQ ID NO: 12; and
sequencing the amplicon to detect the Enterovirus D68.

2. The method of claim 1, wherein the first primer, the second primer, and the third primer include a first universal tail sequence, and wherein the fourth primer and the fifth primer include a second universal tail sequence.

3. The method of claim 2, further comprising adding an index to the amplicon using at least one indexing oligonucleotide, wherein the at least one indexing oligonucleotide comprises a complementary sequence that recognizes at least one of the first universal tail sequence and the second universal tail sequence.

4. The method of claim 3, further comprising sequencing the amplicon using next-generation sequencing.

5. The method of claim 1, wherein the sample comprises a nasopharyngeal swab sample.

6. The method of claim 1, wherein the subject is a human.

* * * * *